(12) United States Patent
Wilkinson et al.

(10) Patent No.: US 11,382,840 B2
(45) Date of Patent: Jul. 12, 2022

(54) METHOD FOR CREATING A MINERAL TRIOXIDE AGGREGATE MATERIAL WITH IMPROVED BIOLOGICAL EFFECTS

(71) Applicant: DENTSPLY SIRONA, Inc., York, PA (US)

(72) Inventors: Kevin Wilkinson, Bixby, OK (US); Geoffrey Ndungu, Tulsa, OK (US)

(73) Assignee: DENTSPLY SIRONA INC., York, PA (US)

( * ) Notice: Subject to any disclaimer, the term of this patent is extended or adjusted under 35 U.S.C. 154(b) by 0 days.

(21) Appl. No.: 17/113,380

(22) Filed: Dec. 7, 2020

(65) Prior Publication Data

US 2021/0106502 A1 Apr. 15, 2021

Related U.S. Application Data

(63) Continuation of application No. 15/972,360, filed on May 7, 2018, now abandoned, which is a continuation
(Continued)

(51) Int. Cl.
*A61K 6/851* (2020.01)
*A61L 27/16* (2006.01)
(Continued)

(52) U.S. Cl.
CPC ............... *A61K 6/851* (2020.01); *A61C 5/50* (2017.02); *A61C 8/0013* (2013.01); *A61C 13/0006* (2013.01); *A61C 13/0835* (2013.01); *A61K 6/17* (2020.01); *A61K 6/76* (2020.01); *A61K 6/887* (2020.01); *A61L 27/165* (2013.01); *A61L 27/30* (2013.01); *A61L 27/306* (2013.01); *A61L 27/32* (2013.01); *B28B 1/14* (2013.01); *B28B 11/24* (2013.01);
*C04B 28/04* (2013.01); *C23C 14/082* (2013.01); *C23C 14/22* (2013.01); *C23C 14/24* (2013.01); *C23C 14/34* (2013.01);
(Continued)

(58) Field of Classification Search
CPC ...... A01L 27/165; A01L 27/06; A01L 27/306; A61K 6/851; A61C 5/50; A61C 8/0013; A61C 13/0835; A61C 13/0006
See application file for complete search history.

(56) References Cited

U.S. PATENT DOCUMENTS

| 8,979,991 B2 | 3/2015 | Torabinejad |
| 2010/0203478 A1* | 8/2010 | Rubbert ............... A61C 8/0018 433/212.1 |
| 2014/0161901 A1 | 6/2014 | Lee |

FOREIGN PATENT DOCUMENTS

EP 2638892 A1 9/2013

OTHER PUBLICATIONS

International Search Report; PCT/US2016/029779; Jul. 11, 2016 (completed); dated Jul. 18, 2016.
(Continued)

*Primary Examiner* — C Melissa Koslow
(74) *Attorney, Agent, or Firm* — Dentsply Sirona Inc.

(57) ABSTRACT

A dental device is improved in its ability to produce hydroxyl apatite by having a layer of mineral trioxide aggregate (MTA) deposited thereon. A tile of MTA is prepared, heat treated and sintered to produce a micronized tile of MTA that can then be deposited by physical vapor depositions, hot isostatic pressing, molding or other conventional technique.

15 Claims, 25 Drawing Sheets
(8 of 25 Drawing Sheet(s) Filed in Color)

Related U.S. Application Data of application No. 15/140,586, filed on Apr. 28, 2016, now abandoned.

(60) Provisional application No. 62/154,282, filed on Apr. 29, 2015.

(51) Int. Cl.
| | |
|---|---|
| *A61L 27/30* | (2006.01) |
| *A61L 27/32* | (2006.01) |
| *A61K 6/17* | (2020.01) |
| *A61K 6/76* | (2020.01) |
| *A61K 6/887* | (2020.01) |
| *A61C 8/00* | (2006.01) |
| *A61C 13/083* | (2006.01) |
| *C23C 14/34* | (2006.01) |
| *C23C 14/24* | (2006.01) |
| *A61C 5/50* | (2017.01) |
| *A61C 13/00* | (2006.01) |
| *C23C 14/08* | (2006.01) |
| *B28B 1/14* | (2006.01) |
| *B28B 11/24* | (2006.01) |
| *C04B 28/04* | (2006.01) |
| *C23C 14/22* | (2006.01) |
| *C04B 103/00* | (2006.01) |
| *C04B 111/00* | (2006.01) |

(52) U.S. Cl.
CPC ....... *A61L 2420/02* (2013.01); *A61L 2420/08* (2013.01); *A61L 2430/12* (2013.01); *C04B 2103/0067* (2013.01); *C04B 2111/00836* (2013.01)

(56) References Cited

OTHER PUBLICATIONS

Written Opinion of the International Searching Authority; PCT/US2016/029779; Jul. 11, 2016 (completed); dated Jul. 18, 2016.
International Preliminary Report on Patentability; PCT/US2016/029779; PCT/US2016/029779; Jul. 11, 2016 (completed); dated Jul. 18, 2016.
"The Biomineralization Ability of Mineral Trioxide Aggregate and Portland Cement on Dentin Enhances the Push-out Strength"; Journal of Endodontics, Lippincott Williams & Wilkins; vol. 36, No. 2; Feb. 1, 2010; pp. 286-291.
"Mineral Trioxide Aggregate: A Comprehensive Literature Rewiew—Part 1: Chemical, Physical, and Antibacterial Properties"; Journal of Endodontics; vol. 36, No. 1; Jan. 2010; pp. 16-27.

* cited by examiner

| Sample ID | Process parameters | | Weight lost (%) | | Volume lost (%) | | Density (g/cm3) | |
|---|---|---|---|---|---|---|---|---|
| | Heating rate (°C/min) | Dwell time (hours) | Mean | Standard Error | Mean | Standard Error | Mean | Standard Error |
| Pressed cement | | | | | | | 2.07 | 0.071 |
| Set 1 | 10 | 8 | 14.8 | 0.013 | 15.3 | 0.29 | 2.21 | 0.183 |
| Set 2 | 2 | 2 | 14.6 | 0.039 | 13.3 | 0.37 | 2.23 | 0.107 |
| Set 3 | 10 | 2 | 14.0 | 0.081 | 10.1 | 1.83 | 2.15 | 0.118 |
| Set 4 | 2 | 8 | 15.1 | 0.036 | 15.6 | 0.42 | 2.35 | 0.355 |

| After calcination | | | | | | | | | |
|---|---|---|---|---|---|---|---|---|---|
| | Ca | Si | Al | P | S | Mg | Na | Fe | Others |
| No calcination | 68.9 | 23.4 | 2.4 | 0.1 | 2.2 | 1.4 | 1.0 | 0.4 | 0.3 |
| p-200 | 69.0 | 23.6 | 2.5 | 0.0 | 2.3 | 1.2 | 0.6 | 0.4 | 0.3 |
| p-470 | 69.0 | 23.6 | 2.5 | 0.1 | 2.2 | 1.3 | 0.6 | 0.4 | 0.3 |
| m1350 | 67.9 | 24.6 | 2.5 | 0.2 | 1.9 | 1.3 | 1.0 | 0.3 | 0.3 |
| m1450 | 69.0 | 25.2 | 2.6 | 0.2 | 0.7 | 1.2 | 0.5 | 0.3 | 0.3 |
| Sintered at 850 °C for 8hr | | | | | | | | | |
| | Ca | Si | Al | P | S | Mg | Na | Fe | Others |
| No calcination | 68.0 | 24.8 | 2.5 | 0.1 | 2.3 | 1.5 | 0.2 | 0.4 | 0.3 |
| p-200 | 68.2 | 24.5 | 2.5 | 0.0 | 2.4 | 1.4 | 0.3 | 0.3 | 0.3 |
| p-470 | 68.0 | 24.9 | 2.5 | 0.1 | 2.3 | 1.5 | 0.1 | 0.4 | 0.2 |
| m1350 | 67.8 | 25.0 | 2.6 | 0.2 | 1.9 | 1.4 | 0.6 | 0.3 | 0.3 |
| m1450 | 68.7 | 25.5 | 2.7 | 0.2 | 0.8 | 1.3 | 0.2 | 0.4 | 0.3 |
| HIP-sintered at 800 °C and 15 ksi for 2hr | | | | | | | | | |
| | Ca | Si | Al | P | S | Mg | Na | Fe | Others |
| No calcination | 68.0 | 24.5 | 2.6 | 0.2 | 1.9 | 1.9 | 0.4 | 0.4 | 0.3 |
| p-200 | 68.5 | 24.5 | 2.5 | 0.1 | 2.1 | 1.4 | 0.4 | 0.3 | 0.2 |
| p-470 | 68.5 | 24.3 | 2.5 | 0.1 | 2.0 | 1.8 | 0.2 | 0.4 | 0.3 |
| m1350 | 68.2 | 24.8 | 2.6 | 0.1 | 1.8 | 1.6 | 0.3 | 0.4 | 0.3 |
| m1450 | 68.9 | 25.4 | 2.7 | 0.2 | 0.7 | 1.1 | 0.3 | 0.3 | 0.3 |

FIG. 7A
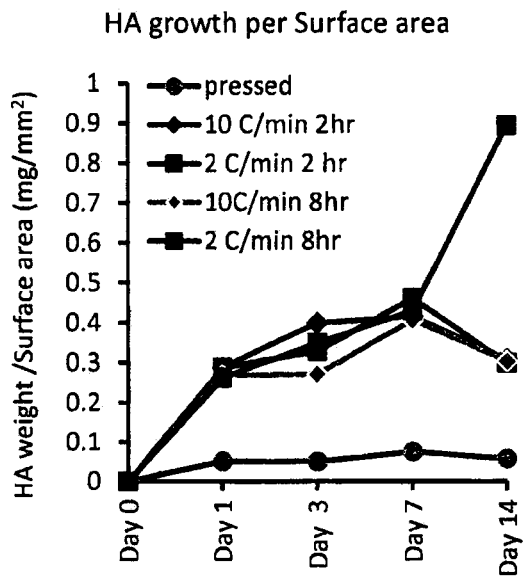
FIG. 7B
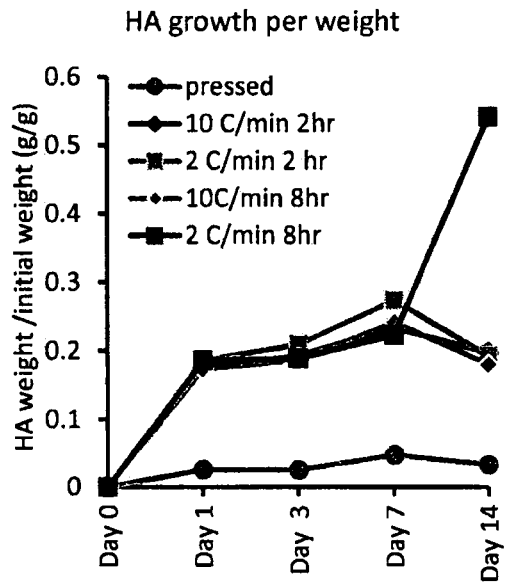
FIG. 7C

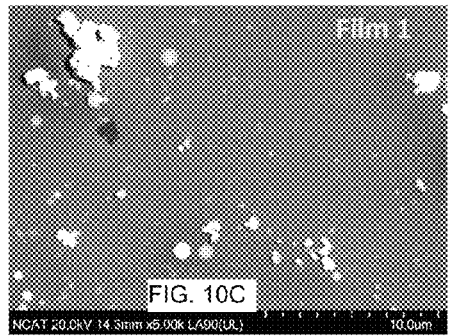
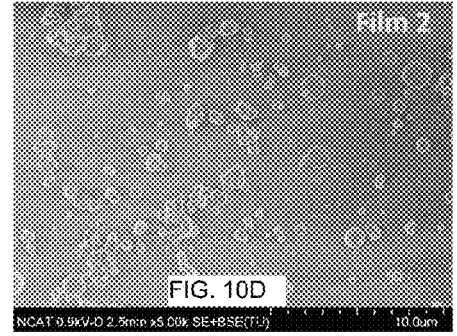
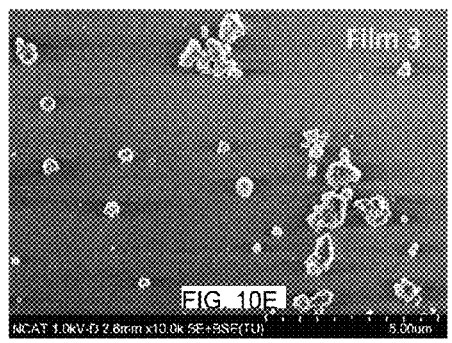
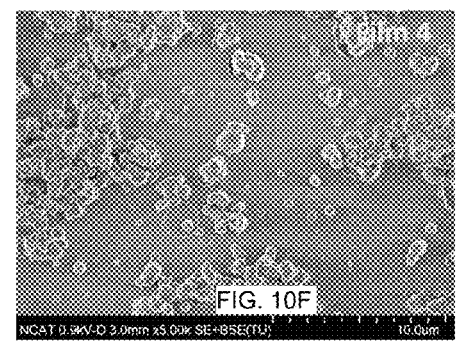
FIG. 10A
| Sample ID | Target | Substrates | Deposition Pressure (mbar) | Laser energy (mJ/pulse) | # of pulses | Film Thickness (nm) |
|---|---|---|---|---|---|---|
| Film 1 | 1(t) | Silicon, gutta percha | 8.6 e-6 | 200 | 20,000 | 378±8 |
| Film 2 | 2(t) | Silicon, gutta percha | 2.3 e-6 | 200 | 20,000 | 344±6 |
| Film 3 | 1(t) | Silicon, gutta percha | 1.9 e-6 | 300 | 20,000 | 510±12 |
| Film 4 | 2(t) | Silicon, gutta percha | 4.6 e-6 | 400 | 20,000 | 489±12 |
FIG. 10B

| Sample ID | PLD Process parameters | | | | Film Thickness (micron) | | | Average Roughness (microns) | | |
|---|---|---|---|---|---|---|---|---|---|---|
| | Laser power | # Pulses | Substrate temperature | W pressure | | | | | | |
| PTi1 | 600mJ | 10000 | RT | 1.2 e-5 mbar | 0.345 | ± | 0.014 | 0.072 | ± | 0.001 |
| PTi2 | 590mJ | 10000 | 400 C | 7.5 e-5 mbar | 0.398 | ± | 0.034 | 0.091 | ± | 0.009 |
| PTi3 | 580mJ | 20000 | RT | 1.2 e-5 mbar | 0.577 | ± | 0.034 | 0.103 | ± | 0.009 |
| PTi4 | 550mJ | 40000 | RT | 1.2 e-5 mbar | 1.025 | ± | 0.054 | 0.124 | ± | 0.015 |
| PTi5 | 550mJ | 10000 | 600 C | 2.5 e-4 mbar | 0.530 | ± | 0.163 | 0.130 | ± | 0.047 |
| PTi6 | 520mJ | 2500 | RT | 1.2 e-5 mbar | 0.051 | ± | 0.001 | 0.004 | ± | 0.002 |

EDS elemental analisys of films

|  | Ca | Si | Al | Na | Mg | Fe | S | P | O | Ti | Others |
|---|---|---|---|---|---|---|---|---|---|---|---|
| Ti substrate | 0.1 | 0.9 | 0.0 | 0.0 | 0.0 | 0.0 | 4.6 | 0.0 | 0.0 | 74.1 | 20.4 |
| PTi1 | 6.0 | 2.4 | 0.3 | 0.0 | 0.1 | 0.2 | 2.5 | 0.0 | 55.6 | 26.1 | 6.9 |
| PTi2 | 6.0 | 3.3 | 0.4 | 0.1 | 0.2 | 0.2 | 2.7 | 0.0 | 51.1 | 28.0 | 8.0 |
| PTi3 | 13.0 | 4.5 | 0.7 | 0.2 | 0.3 | 0.2 | 1.7 | 0.0 | 58.9 | 15.8 | 4.8 |
| PTi4 | 13.0 | 6.5 | 0.9 | 0.0 | 0.3 | 0.1 | 0.7 | 0.0 | 58.3 | 15.6 | 4.5 |
| PTi5 | 13.3 | 3.9 | 0.5 | 0.0 | 0.1 | 0.2 | 1.7 | 0.0 | 54.3 | 20.8 | 5.1 |
| PTi6 | 1.8 | 0.7 | 0.1 | 0.0 | 0.0 | 0.2 | 3.9 | 0.0 | 38.1 | 42.9 | 12.3 |

| | P | S | Al | Na | Mg | Si | Ca | Ti | Others |
|---|---|---|---|---|---|---|---|---|---|
| Ti substrate | 0.0 | 7.8 | 0.6 | 0.0 | 0.1 | 0.9 | 0.4 | 83.6 | 6.7 |
| PTi1 | 0.0 | 7.0 | 0.9 | 0.3 | 0.1 | 3.9 | 3.9 | 78.9 | 5.1 |
| PTi2 | 0.0 | 7.0 | 0.9 | 0.3 | 0.1 | 3.9 | 3.9 | 78.9 | 5.1 |
| PTi3 | 0.0 | 5.8 | 1.1 | 0.7 | 0.6 | 5.7 | 5.7 | 74.8 | 5.5 |
| PTi4 | 0.0 | 4.9 | 1.2 | 0.6 | 0.6 | 8.8 | 8.8 | 69.6 | 5.5 |
| PTi5 | 0.0 | 5.8 | 1.0 | 0.4 | 0.4 | 5.7 | 5.7 | 75.6 | 5.3 |
| PTi6 | 0.0 | 7.1 | 0.4 | 1.5 | 0.2 | 1.4 | 1.9 | 82.8 | 4.9 |

```
Spectrum: Acquisition
Element    Series   unn. C  norm. C  Atom. C  Error
                    [wt.%]  [wt.%]   [at.%]   [wt.%]
-------------------------------------------------------
Oxygen     K-series  34.10   44.34    59.01    6.2
Sodium     K-series  16.45   21.39     9.81    1.2
Magnesium  K-series   0.14    0.18     0.16    0.1
Silicon    K-series   0.55    0.72     0.55    0.1
Phosphorus K-series  12.58   16.36    11.25    0.6
Calcium    K-series  10.38   13.50    17.17    0.4
Chlorine   K-series   1.47    1.91     1.15    0.1
Aluminium  K-series   0.07    0.09     0.07    0.0
Sulfur     K-series   0.15    0.20     0.13    0.1
Potassium  K-series   1.01    1.31     0.72    0.1
-------------------------------------------------------
           Total:    76.90  100.00   100.00
```

HA formation:
The elemental maps clearly shown that Ca, P and O create a similar patterns. At the same time the Na doesn't have distribution similar to P therefore we can conclude that major component is calcium phosphates.
FIG. 21A
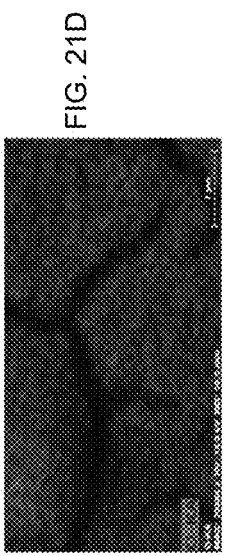
FIG. 21C
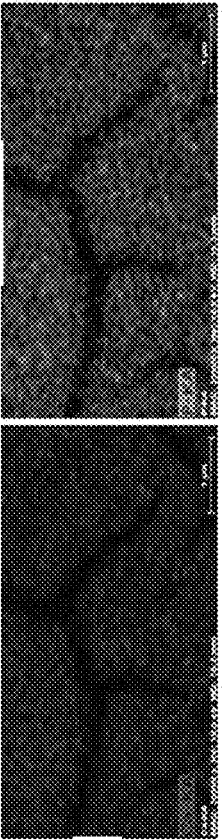
FIG. 21B
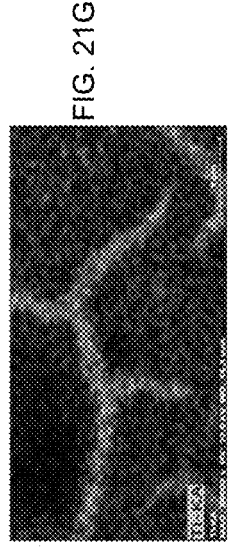
FIG. 21D
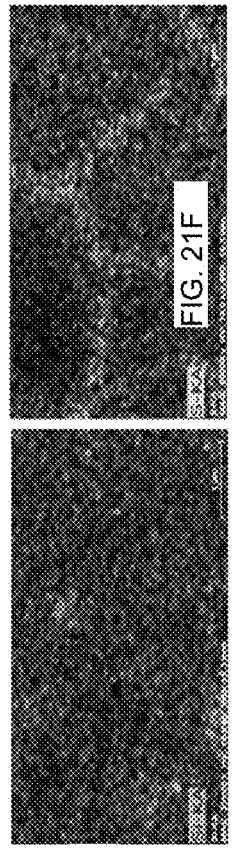
FIG. 21F
FIG. 21E
FIG. 21G
FIG. 21I
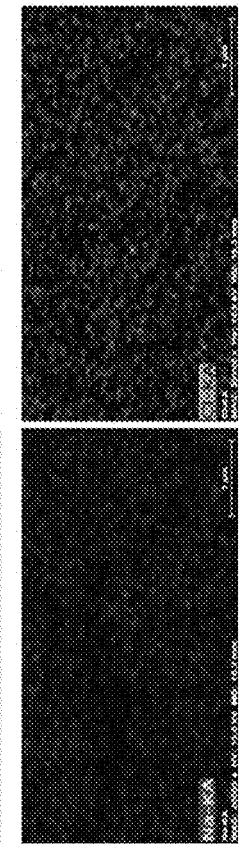
FIG. 21H

METHOD FOR CREATING A MINERAL TRIOXIDE AGGREGATE MATERIAL WITH IMPROVED BIOLOGICAL EFFECTS

RELATED U.S. APPLICATION DATA

This application is a continuation of U.S. non-provisional patent application Ser. No. 15/972,360, filed on May 7, 2018 (now abandoned), which is continuation of U.S. non-provisional patent application Ser. No. 15/140,586, filed on Apr. 28, 2016 (now abandoned), which claims priority to provisional U.S. Pat. App. Ser. No. 62/154,282 filed on Apr. 29, 2015, which are herein incorporated by reference for all purposes.

FIELD OF INVENTION

The present invention relates to the process of creating an improved biological Mineral Trioxide Aggregate (MTA) in a dense tile, or Target. The Target enables a process of coating the improved MTA on implantable medical devices or can be micronized into a MTA material for traditional use.

BACKGROUND OF THE INVENTION

Mineral trioxide aggregate (MTA) (sold under the trade names gray or white ProRoot MTA (Dentsply Sirona Inc., York, Pa., US) is a substance currently used in general dentistry and in endodontics to replace natural tooth material in apexification, pulp capping, pulpotomy, regenerative endodontics, root canal filling, root-end filling, root perforation repair, tooth restorations and the like. An example of MTA used in endodontic applications is disclosed in U.S. Pat. No. 8,979,991 which is hereby incorporated by reference for such disclosure.

It would be desirable to provide an MTA material for dental applications including for endodontic, restorative or other uses that has improved biological effect. More particularly, it would be beneficial to the dental arts to provide such a material that is demonstrated to improve the production of hydroxyl apatite (HA) in the presence of body fluids (or simulated body fluids such as phosphate buffered saline) to produce a material having cementum qualities.

For example, in endodontic applications, the material or composition should provide a stable barrier to bacteria and fluid leakage in the root canal system of a tooth. In addition, the composition should help promote the growth of the new bone and tissue surrounding the root tip area.

BRIEF DESCRIPTION OF THE DRAWINGS

The patent or application file contains at least one drawing executed in color. Copies of the patent or patent application publication with color drawing(s) will be provided by the Office upon request and payment of the necessary fee.

FIG. 7A includes a photo (FIG. 7D-7ZB) representing hydroxyapatite (HA) forming ability sintered cement with the prospective immersion time. The thermally heated cement produces 10 times more HA during immersion in PBS.

FIG. 7B shows a chart representing the results of weight analysis of HA forming ability per surface area of the sintered cement immersed in SBF.

FIG. 7C shows a chart representing the results of weight analysis of HA forming ability per weight of the sintered cement immersed in SBF.

FIG. 10A depicts SEM micrographs (FIG. 10C-10F) of films deposited on silicon substrate by PLD process at different laser energies.

FIG. 10B depicts a table of PLD process parameters used for deposition of films presented in FIG. 10A.

FIG. 12B includes a table of PLD process parameters used for deposition of MTA films on titanium implants shown in FIG. 12A.

FIG. 21A includes SEM micrograph of the area analyzed with EDS spectrum mapping of HA formed on MTA coating deposited on titanium after 21 day of immersion in SBF.

FIG. 21B includes a photo representing Ca-Ka portion of the EDS map of HA formed on MTA coating deposited on titanium after 21 day of immersion in SBF.

FIG. 21C includes a photo representing P-Ka portion of the EDS map of HA formed on MTA coating deposited on titanium after 21 day of immersion in SBF.

FIG. 21D includes a photo representing O-Ka portion of the EDS map of HA formed on MTA coating deposited on titanium after 21 day of immersion in SBF.

FIG. 21E includes a photo representing Si-Ka portion of the EDS map of HA formed on MTA coating deposited on titanium after 21 day of immersion in SBF.

FIG. 21F includes a photo representing S-Ka portion of the EDS map of HA formed on MTA coating deposited on titanium after 21 day of immersion in SBF.

FIG. 21G includes a photo representing Ti-Ka portion of the EDS map of HA formed on MTA coating deposited on titanium after 21 day of immersion in SBF.

FIG. 21H includes a photos representing Na-Ka portion of the EDS map of HA formed on MTA coating deposited on titanium after 21 day of immersion in SBF.

FIG. 21I includes a photo representing Cl-Ka portion of the EDS map of HA formed on MTA coating deposited on titanium after 21 day of immersion in SBF.

SUMMARY OF THE INVENTION

A dense Mineral trioxide aggregate (MTA) tile is produced through a series of process steps which creates a Target suitable for physical vapor deposition (PVD) methods. The resulting MTA material (Target) has improved biological effects and produces hydroxyapatite (HA) at an accelerated rate when immersed into simulated body fluid. The resulting Target can be used to deposit a thin layer as desired, such as upon an obturation point, or can be micronized to use as powder in sealer mixture or as additive to gutta-percha resin during compression molding and/or injection molding process. Conventional obturation points such as those made of gutta percha materials are useful in the application of the present invention.

According to one embodiment of the invention, a thin layer of a processed MTA was deposited using PVD method on the surface of otherwise conventional gutta-percha points. Both processed MTA (Target) and thin layer deposited from Target produces hydroxy apatite mineral in the presence of Phosphate Buffered Saline which is beneficial in the formation of cementum like material for natural sealing of dental root canals.

Another embodiment comprises the use of micronized Target molded onto the surface of a gutta-percha point using a compression molding technique.

A further embodiment of the invention includes the use of micronized Target molded onto the surface of the gutta-percha using an injection molding technique.

Another preferred embodiment is deposition of processed MTA (Target) in a form of thin film onto implantable and prosthetic devices using PVD methods.

DETAILED DESCRIPTION OF THE INVENTION

Figure 1:
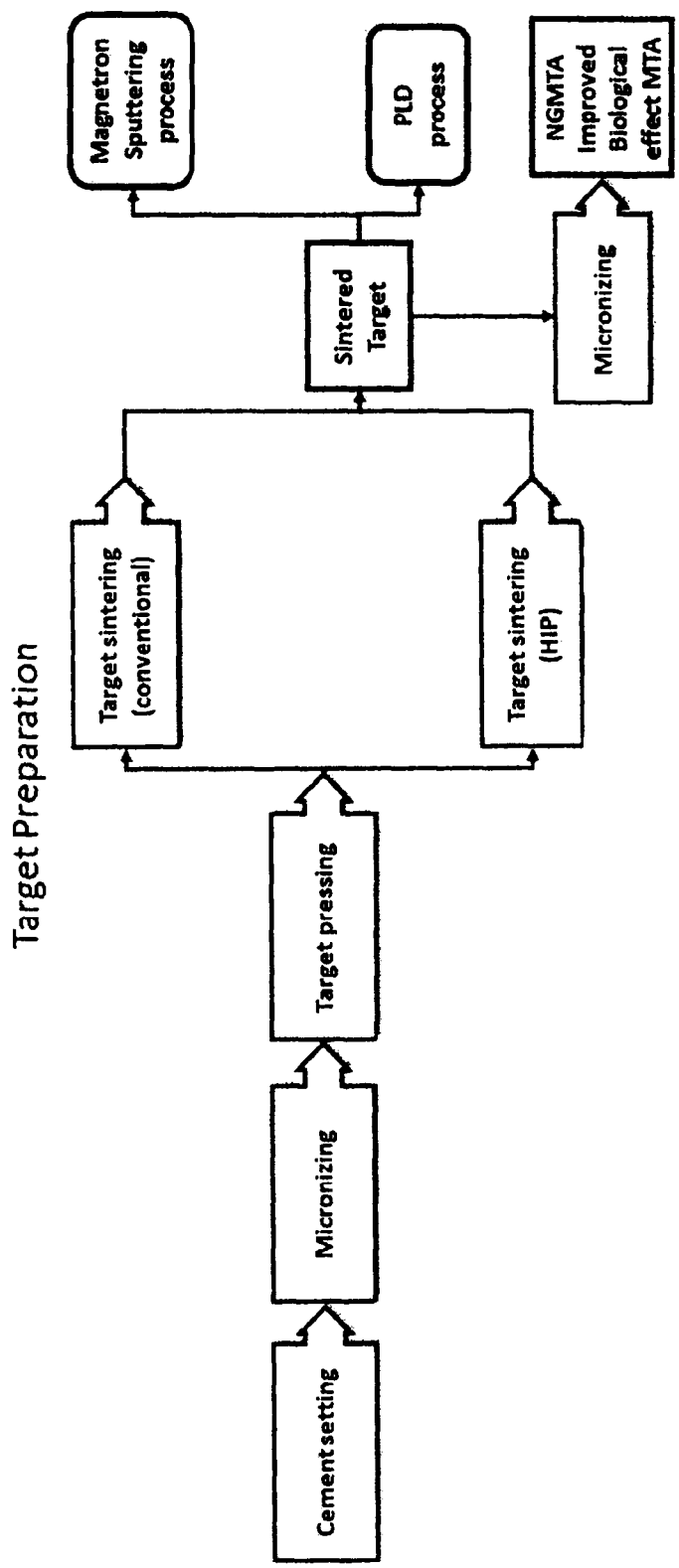
FIG. 1 includes a flowchart of a target preparation process.

A dense MTA with improved biological effects is produced through special processing techniques including: setting which includes steps of : (i) mixing distilled water and cement, weight ratio 1/3; (ii) placing mixture in a mold; (iii) placing the mold in in a humidity chamber [$CO_2$ 6000] Humidity 90%, Temperature 36° C. for 48 hours; (iv) Baking in oven (temperature 160° C. for 6 hours), micronization which includes steps of (i) Grinding [COL-INT-Tech] and/or (ii) Ball milling [SPEX Sample Prep Mixer/Mill 8000M: Zirconia or alumina ball, alcohol can be used as liquid media, Milling for 15-30 minutes, particles size below 53 micron, Target/powder pressing, which include Green compacts pressing {carver hydraulic press #3925: Circular dies for compact pressing, diameters 13 mm, 31 mm and 50 mm; applied pressure up to 90 Psi and Sintering (a) Conventional [Conventional furnace [Carbolite BLF-1700}: Ramp 2.5° C./min to 180° C.; Dwell@180° C. for 15-30 min; Ramp 2.5° C./min to 450° C., Dwell@450° C. for 30 min-1 hr. Ramp 2.5° C./min to 850° C., Dwell@850° C. for 8-24 hrs] (b) HIP (Hot lsostatic Press (AIP6-30H]: Ramp 10° C./min to 180° C., vacuum: Dwell@180° C. for 15 min, vacuum; Ramp 10° C./min to 450° C., vacuum; Dwell@450° C. for 30 min, up to 5 ksi; Ramp 5° C./min to 750° C., up to 10 ksi Dwell@750° C. for 1-4 hrs, 10-20 ksi. (FIG. 1). The resulting dense MTA material has improved biological effects and in the presence of simulated body fluid and produces HA at an increased and accelerated rate.

Dense MTA targets can be created for use in physical vapor deposition (PVD) methods to create a thin layer of MTA material on the surface of implantable devices such as dental implants, endodontic obturation materials and the like. PVD techniques include:

Cathodic Arc Deposition: In which a high-power electric arc discharged at the target (source) material blasts away some into highly ionized vapor to be deposited onto the work piece.

Electron beam physical vapor deposition: In which the material to be deposited is heated to a high vapor pressure by electron bombardment in "high" vacuum and is transported by diffusion to be deposited by condensation on the (cooler) work piece.

Evaporative deposition: In which the material to be deposited is heated to a high vapor pressure by electrically resistive heating in "low" vacuum.

Pulsed laser deposition: In which a high-power laser ablates material from the target into a vapor.

Sputter deposition: In which a glow plasma discharge (usually localized around the "target" by a magnet) bombards the material sputtering some away as a vapor for subsequent deposition.

A thin layer of MTA (Mineral Trioxide Aggregate) was deposited from sintered targets on the surface of gutta percha points and titanium implantable device. The processed MTA material may also be ground into small particles for use in Dental products or as a MTA powder with improved biologicals effects.

The improved MTA is particularly suitable for obturating and sealing dental root canals. The improved MTA provides a stable barrier to bacterial and fluid leakage in the root canal. The accelerated generation of HA will also help promote the growth of new bone and tissue surrounding the root tip area. The improved MTA should also provide a stable barrier to bacteria and fluid leakage in the root canal system of the tooth.

Target Creation Process

A method for forming the dense MTA material (Target) may include one or more of the steps/processes described below and further shown in FIG. 1

Mixing Process

Mixing (white) Portland Cement (WPC or PC) to Deionized water having a ratio in the range of about 10:1 to about 1:10, preferably about 5:1 to about 1:5, and more preferably about 5:1 to about 1:1 (e.g., about 3:1 such as about 3 parts PC (WPC) to about 1 part deionized water). The mixture is thoroughly blended and vacuum is drawn out to create harmonized cake mix and then placed in molds.

Curing Process

Once the mixed cement is put in molds, the molds are placed in a humidity chamber to cure. The humidity chamber is set at 36° C. with 90% Relative Humidity (RH) from about 5 hours to about 10 days, and preferably from about 12 hours to about 5 days (e.g., about 2 days).

Post Cure Baking Process

Once the cement is cured, the set cement is placed in a Post cure bake oven set at a temperature from about 50° C. to about 500° C., and preferably from about 100° C. to about 250° C. (e.g., about 160° C.) for a time ranging from about 15 mins to about 2 days, and preferably from about 1 hour to about 12 hours (e.g., about 6 hours).

Ball Milling and Micronizing Process

The target creation process may include a micronizing step. Once the cement is post baked, it is then pulverized, micronized and sieved to a particle size ranging from about 1 micron to about 200 microns, and preferably from about 10 microns to about 100 microns (e.g., about 53 microns ($\mu 53$)).

Sintering Process

Figures 2A, 2B:
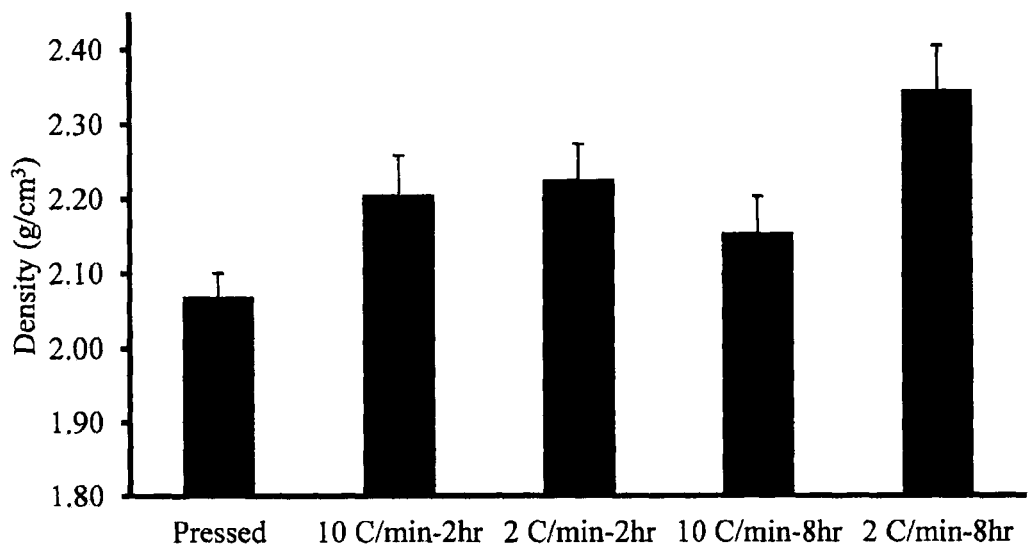
FIG. 2A includes a table providing data of the effects of sintering parameters on target density.
FIG. 2B includes a chart representing the effect of sintering parameters on targets density shown in the table of FIG. 2A. Lower heating rate and longer dwell time leads to higher density. There was no significant changes in elemental composition due to sintering. It was also shown that heat treated WPC produced 10 times more HA when immersed in SBF.

The target creation process may include a Sintering Step. The Powder Micronized MTA is pressed into a green compacts using a hydraulic press with the applied pressure range from 60 Psi to 120 Psi. The green compacts are placed into a sintering chamber for a heat treatment that consists of several heating steps/stages. The first stage is heating up to the temperature range from about 25° C. to about 200° C., preferably from about 100° C. to about 150° C. (e.g., about 125° C.) and dwell at this temperature for a time period of 5 mins to about 5 hours, preferably from 15 mins to about 2 hours (e.g., about 30 to about 40 mins). The second stage of heat treatment, includes the temperature to range from about 275° C. to about 650° C., and preferably from about 350° C. to about 525° C. (e.g., about 450° C.) for a time period ranging from about 5 minutes to about 5 hours, and preferably from about 15 mins to about 3 hours (e.g., about 1 to 2 hours). At the final step of the sintering process, the temperature ranging from about 550° C. to about 1100° C., and preferably from about 650° C. to about 975° C. (e.g., about 750° C. to 850° C.) for a period of time ranging from about 30 mins to about 2 days, and preferably from about 2 hours to about 1 day (e.g., about 4 hours to about 12 hours). The overall sintering process can be completed in one step at the temperature range about 750° C.-850° C. with the slow heating ramp and longer dwell time. The effect of sintering parameters on density of sintered MTA (Target) is shown in table and graph presented on FIG. 2A and FIG. 2B). The highest density of sintered target was achieved at the lowest heating rate and longer dwell time.

HIP Process

Figure 3:
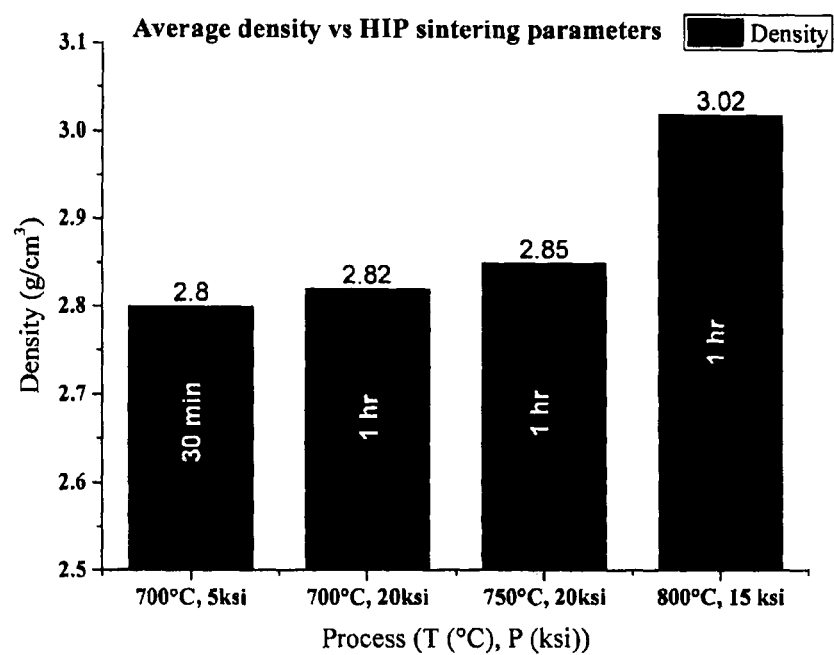
FIG. 3 includes a chart representing the effect of HIP process parameters on targets density. The green compact preparation procedure (additional ball-milling, pressing in carver press at 90-120 Mpa) has the highest impact on density of sintered ceramics (samples h1-h7, p=1.8-2.4 $g/cm^3$ vs p>2.6 g/cm); HIP: Process temperature has higher impact on density than pressure.

The target creation process may include a hot isostatic pressing (HIP) step/process. The set sintered targets may be placed into a HIP chamber at a temperature ranging from about 250° C. to about 1500° C., and preferably from about 500° C. to about 1000° C. (e.g., about 750° C. to about 850° C.) for a period of time ranging from about 30 mins to about 2 days, and preferably from about 2 hours to about 1 day (e.g., about 4 hours to about 12 hours) at a pressure ranging from about 1,000 psi to about 50,000 psi, and preferably from about 7,500 psi to about 35,000 psi (e.g., about 15,000 psi to 20,000 psi). The effect of HIP sintering parameters on density of sintered MTA (Target) is shown in FIG. 3. The highest density of HIP-sintered target was achieved at higher temperature and moderate pressure inside HIP chamber.

Figure 4A:
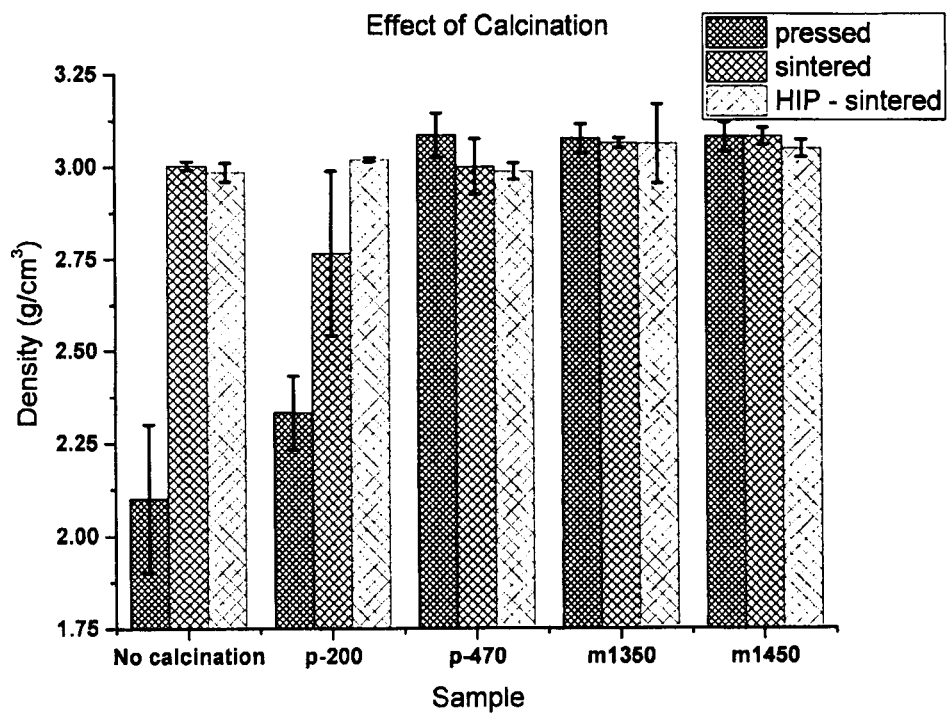
FIG. 4A includes a chart representing the effect of pre-calcination on targets density. Calcination (heat treatment of powder before ball-milling and pressing in order to remove $CO_2$ and water) at temperatures above 450° C. help to achieve similar densities for HIP and conventional sintering.
Figure 4B:
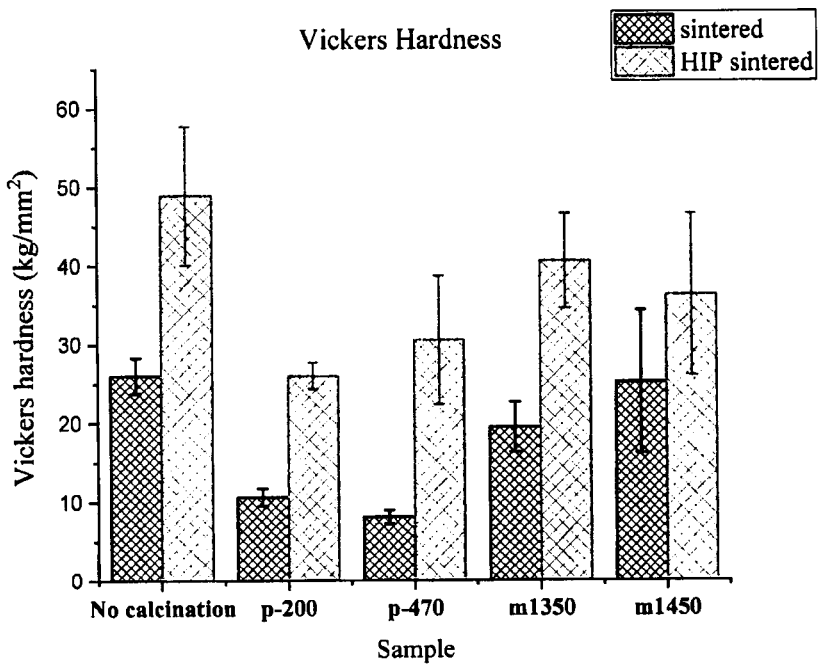
FIG. 4B includes a chart representing the effects of sintering parameters on mechanical properties on target. There is a significant difference in Vickers hardness (VH) between conventional and HIP sintering samples. The VH of HIP-sintered samples is 30-50% higher. However, the calcination before sintering doesn't improve hardness of sintered cement (both conventional and HIP-sintered).
Figure 5A:
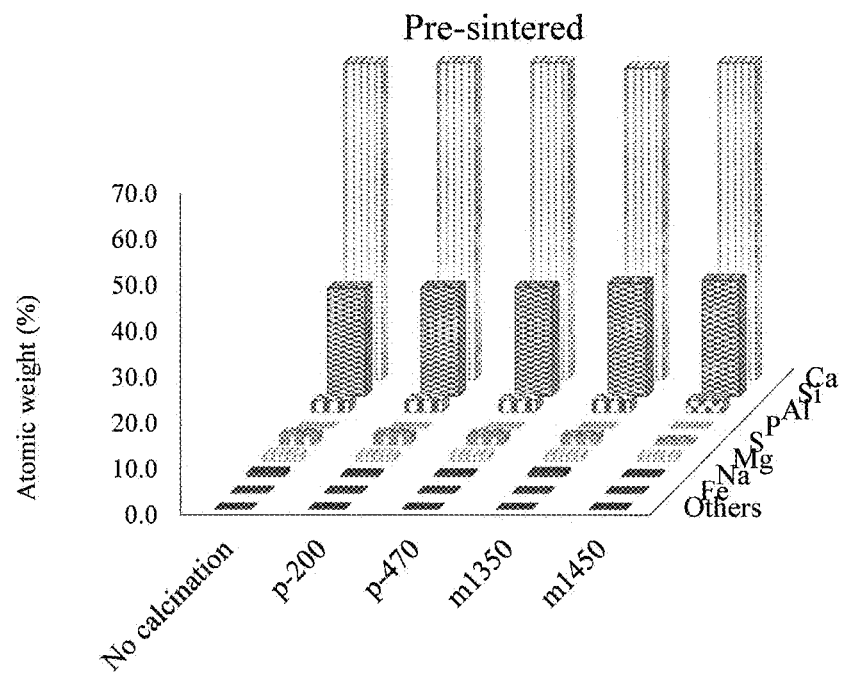
FIG. 5A includes a chart representing the effects of pre-calcination on elemental composition of pre-sintered target.
Figure 5B:
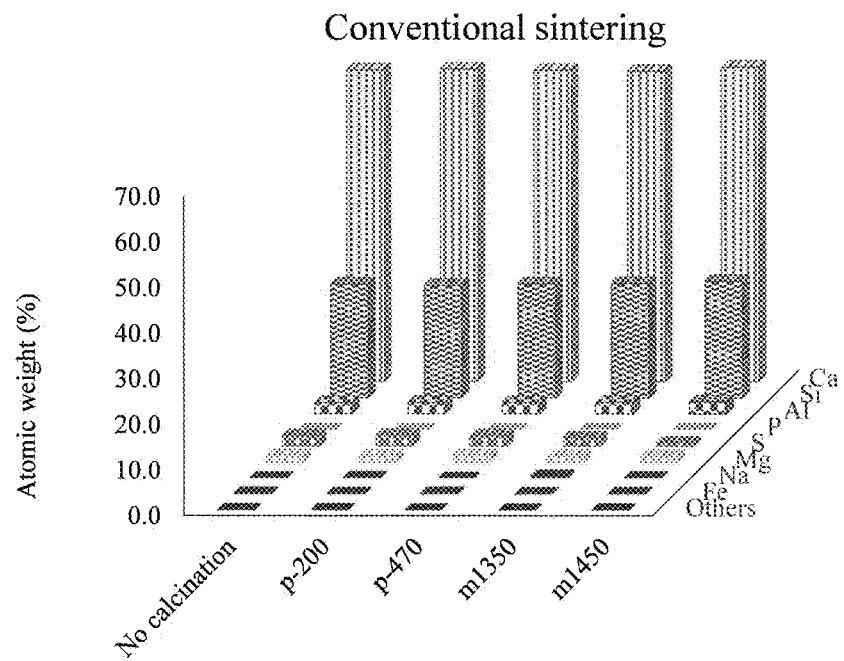
FIG. 5B includes a chart on the effects of pre-calcination on elemental composition of a conventional sintered target.
Figures 5C, 5D:
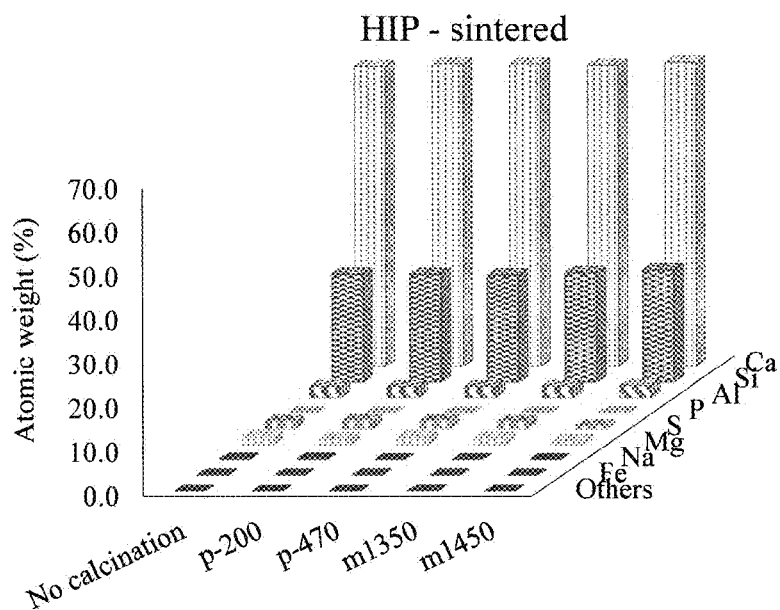
FIG. 5C includes a chart on the effects of pre-calcination on elemental composition of a HIP sintered target.
FIG. 5D includes a table representing the data of the effects of pre-calcination and sintering parameters on elemental composition of target. Calcination: there is no significant changes in Ca, Si content. Reduction in S. There is no significant changes in elemental composition after conventional or HIP sintering.

The pre-calcination process that reported to be an improvement for density and mechanicals properties of sintering ceramics doesn't have a significant effect on properties of MTA as can be seen from graphs presented on FIGS. 4A and 4B.

Figure 6A:
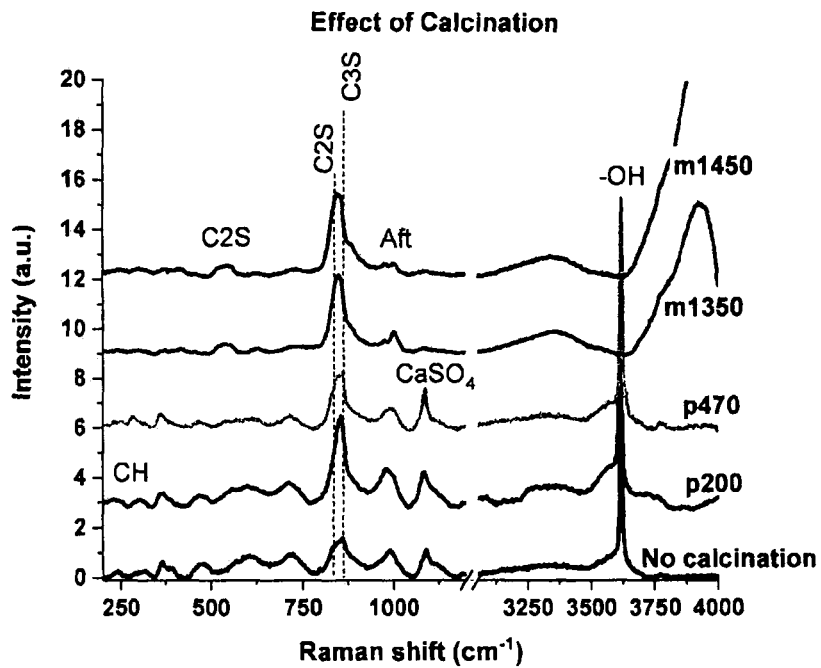
FIG. 6A depicts Raman spectra of the effect of pre-calcination on on phase composition of target.
Figure 6B:
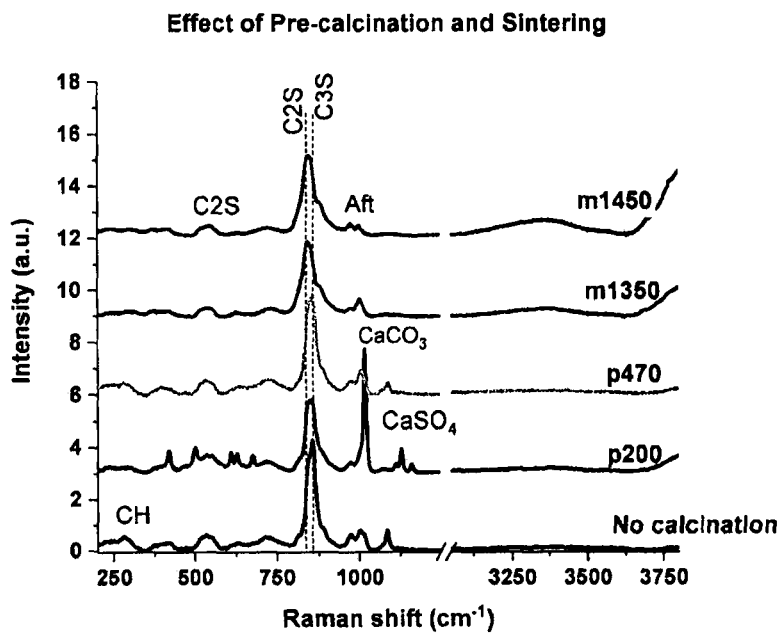
FIG. 6B depicts Raman spectra of the effect of pre-calcination and conventional sintering parameters on phase composition of target.
Figure 6C:
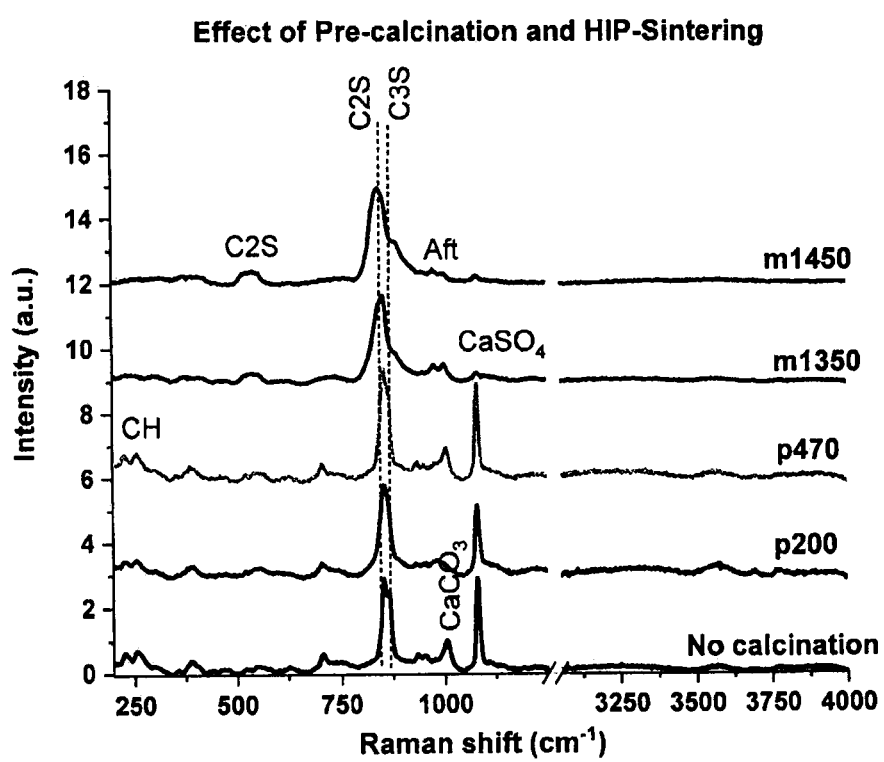
FIG. 6C depicts Raman spectra of the effect of pre-calcination and HIP sintering parameters on phase composition of target. The melting process: removes hydrated phases, $CaCO_3$ and $CaSO_4$; partially transforms C3S to C2S.

The changes in chemical composition in MTA material during sintering processes described above were monitored using Raman spectroscopy and X-Ray Florescence spectroscopy (XRF). The Raman analysis indicates that pre-calcination heat treatment affect the degree of hydration and with the high calcination temperature (lines m1350 and m1450 on FIG. 6A) the water and hydrated phases completely removed. Both HIP and conventional sintering not only removed the water and hydrated phases from sintered MTA but also changed the balance between tricalcium (C3S) and dicalcium (C2S) silicates (FIGS. 6B and 6C). However, there was no significant changes in elemental composition were detected with the XRF analysis (presented on graphs and table as shown in FIGS. 5A-D).

The sintered MTA targets may also be further micronized to a particle size ranging from about 1 micron to about 200 microns, and preferably from about 10 microns to about 100 microns (e.g., about 53 microns). The resultant powder MTA has improved biological effects and produces HA at an accelerated rate, so it can be used as additive to existing dental sealers to improve biocompatibility and osteointegration process.

Compression molding process which entails sprinkling MTA powder on the substrate during compression molding process; and powder spraying process which, entails blasting the substrate with high velocity spray of MTA powder. The substrates includes gutta percha point and titanium implantable device.

The preferred method of coating medical devices with MTA target is physical vapor deposition such as Pulsed Laser Deposition (PLD) or RF Magnetron Sputtering. Alternative methods of creating coating from dense MTA target may also include E-beam and thermal evaporations like is discussed above.

Pulsed Laser Deposition (PLD)

This is a thin film deposition technique where a high-power pulsed laser beam is focused inside a vacuum chamber to strike a target of the material that is to be deposited. This material is vaporized from the target (in a plasma plume) which deposits it as a thin film on the substrate (in this case the GP points); this process occurs in ultra-high vacuum.

Figure 8:
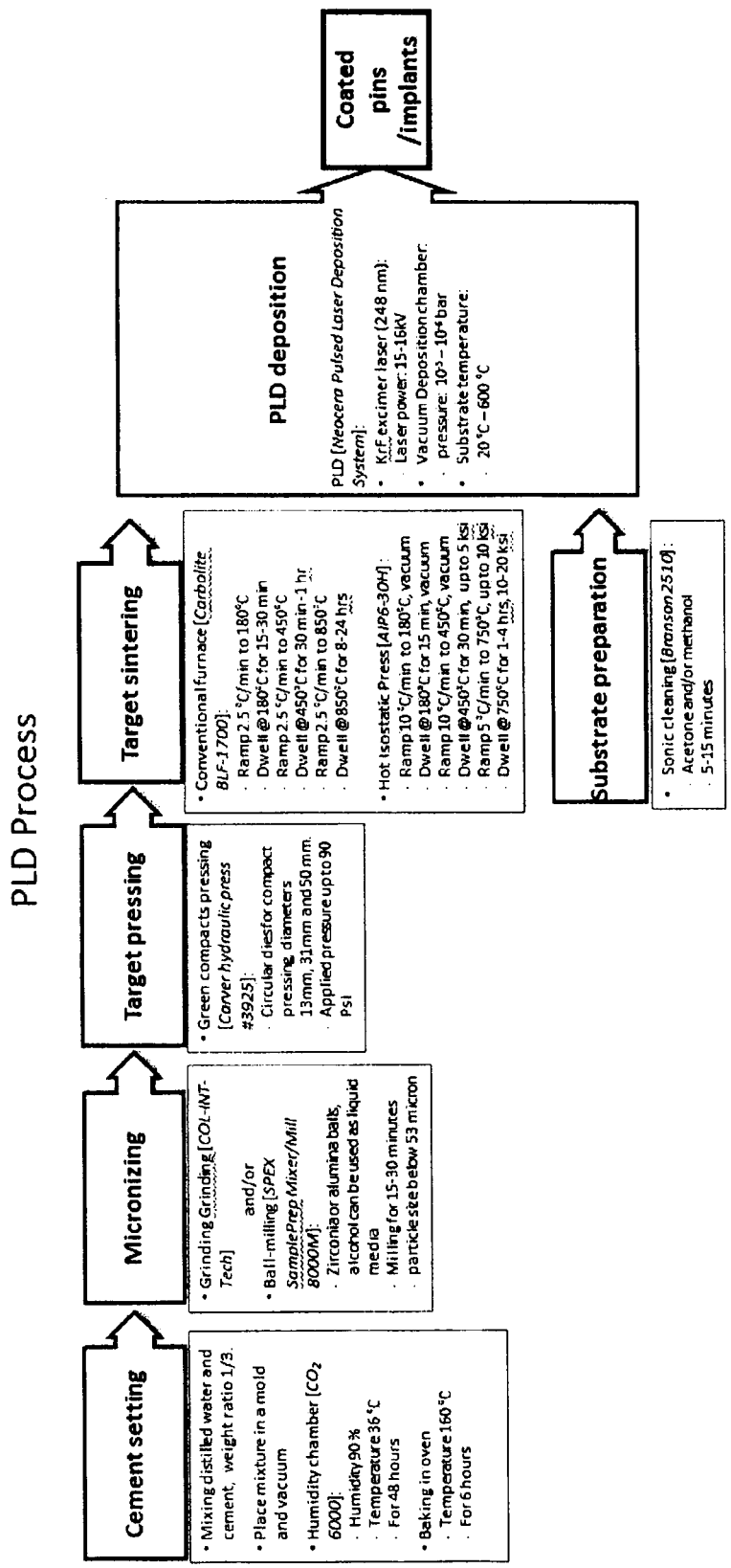
FIG. 8 includes a flowchart of a PLD process.

While the basic-setup is simple relative to many other deposition techniques, the physical phenomena of laser-target interaction and film growth are quite complex. When the laser pulse is absorbed by the target, energy is first converted to electronic excitation and then into thermal, chemical and mechanical energy resulting in evaporation, ablation, plasma formation and even exfoliation. The ejected species expand into the surrounding vacuum in the form of a plume containing many energetic species including atoms, molecules, electrons, ions, clusters, particulates and molten globules, before depositing on the substrate. The general workflow of manufacturing MTA thin film with the PLD process presented on FIG. 8.

Magnetron Sputtering

RF (Radio-Frequency) Magnetron Sputtering is a plasma-assisted method for physical vapor deposition of thin films. RF source utilizes high power voltage pulses (impulses) of with the fixed frequency of 13.6 MHz.

The RF-sputtering technique offer an advantage of depositing nonconductive materials onto substrate at low deposition temperatures.

Figure 9:
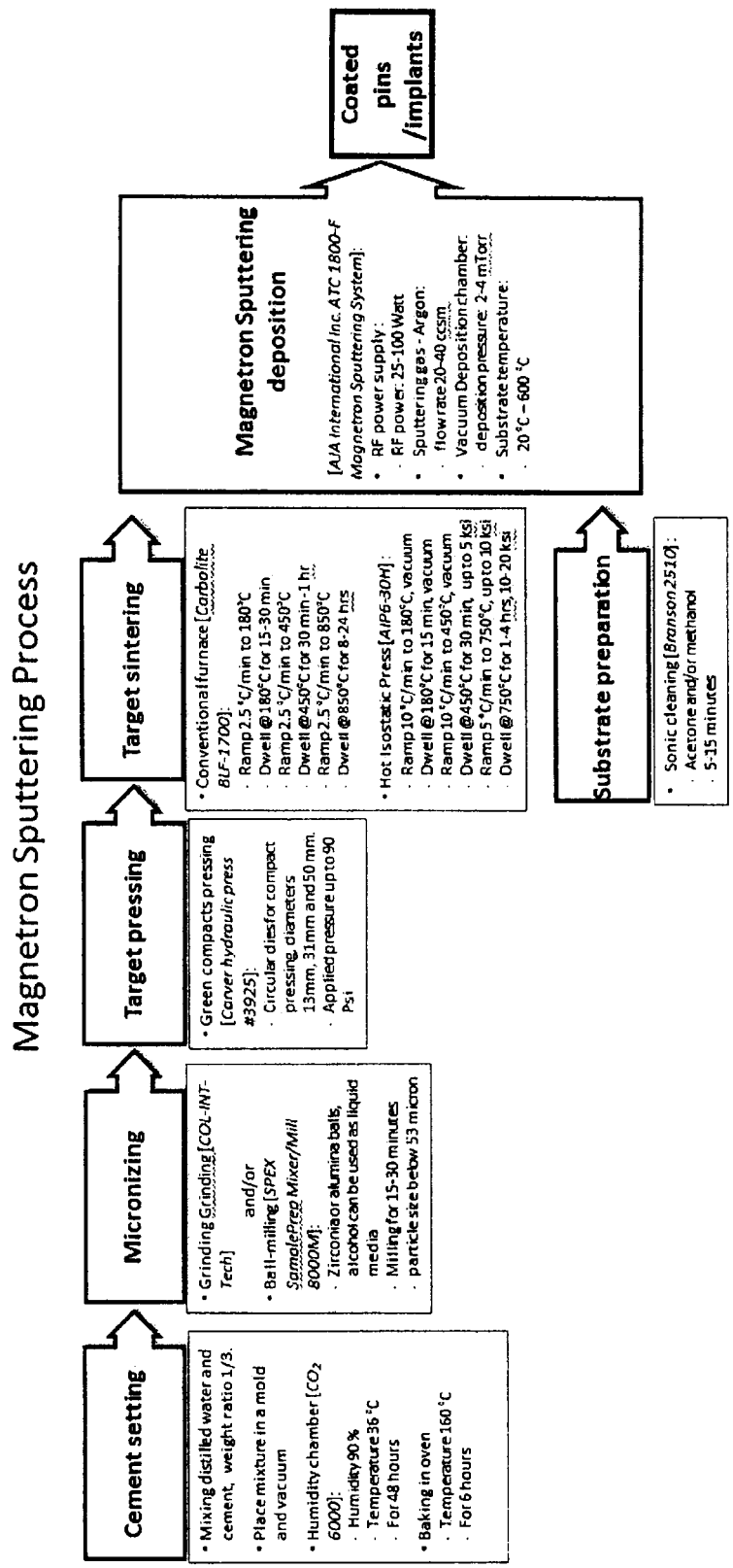
FIG. 9 includes a flowchart of a magnetron spattering process.

The general workflow of manufacturing MTA thin film with the magnetron sputtering process is depicted in FIG. 9.

Figure 11:
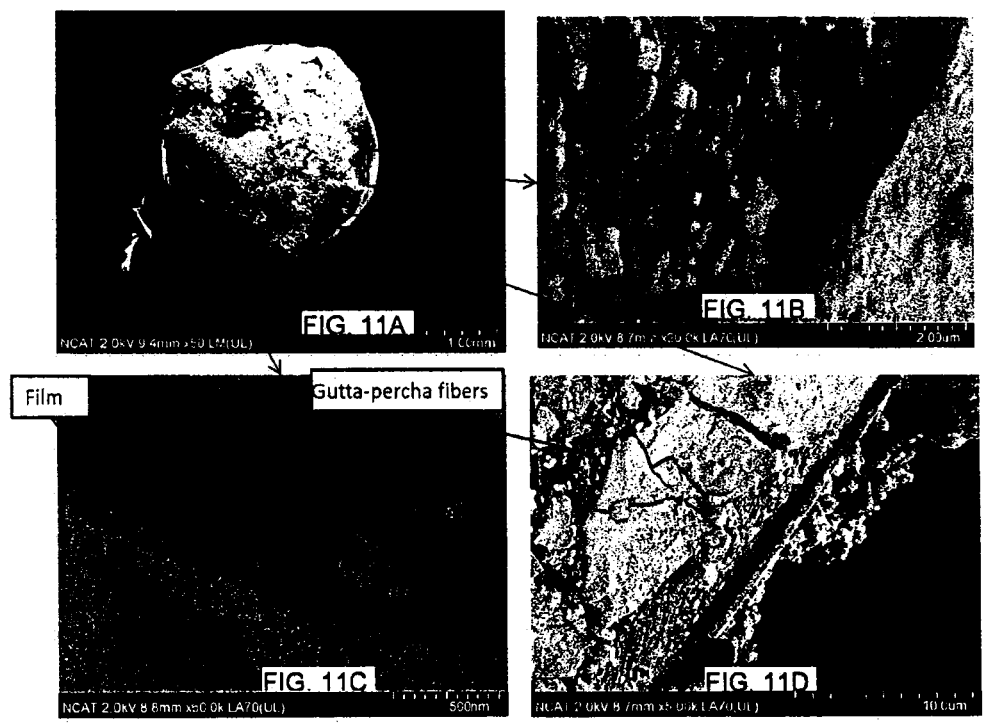
FIG. 11 depicts SEM micrographs (FIG. 11A-11D) of cross-section of a gutta-percha points coated by MTA film deposited with the PLD process.
Figures 12, 12A:
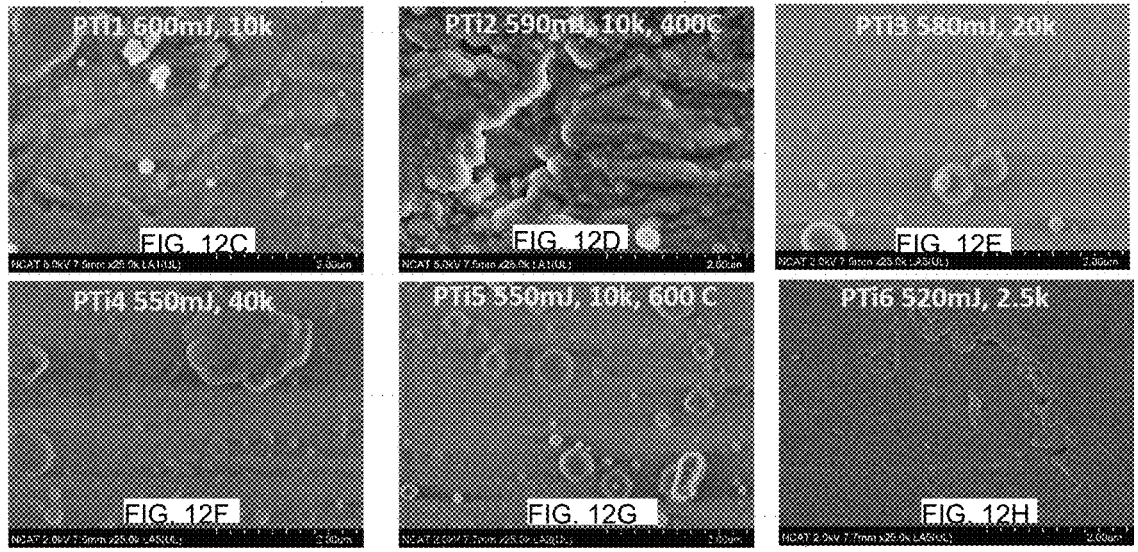
FIG. 12A depicts SEM micrographs (FIG. 12C-12H) of MTA films on a titanium implant deposited by PLD process.
Figure 13A:
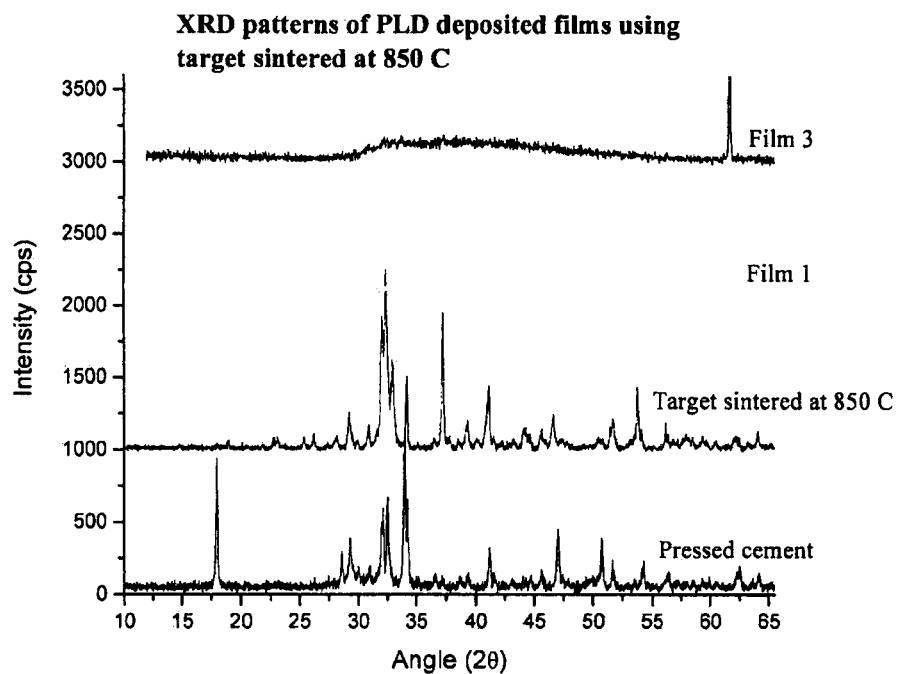
FIG. 13A includes a chart representing X-Ray analysis, which confirms amorphous structure of films observed in FIG. 10A-B.
Figure 13B:
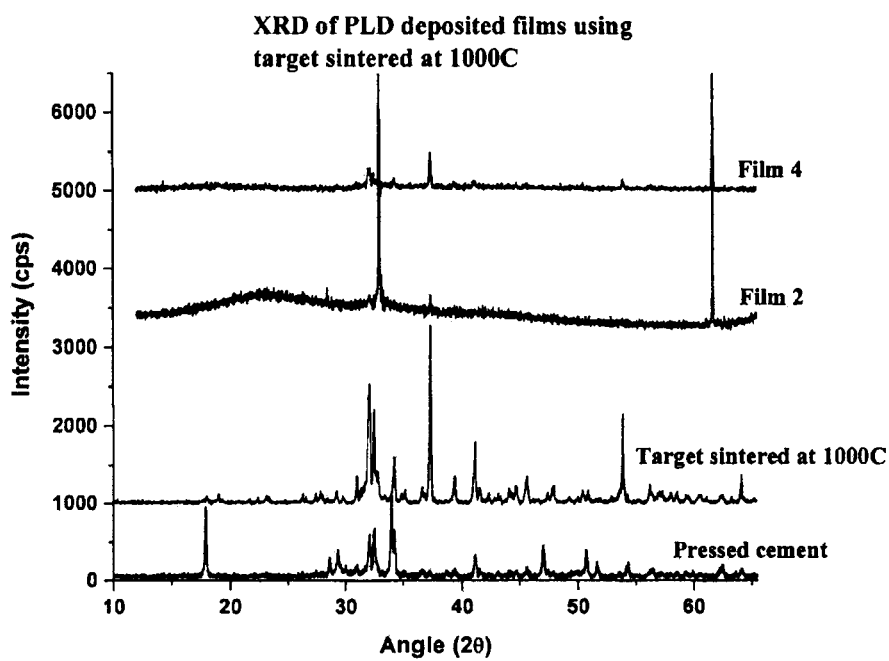
FIG. 13B includes a chart representing X-Ray analysis, which confirms amorphous structure of films observed in FIG. 10A-B.
Figure 14A:
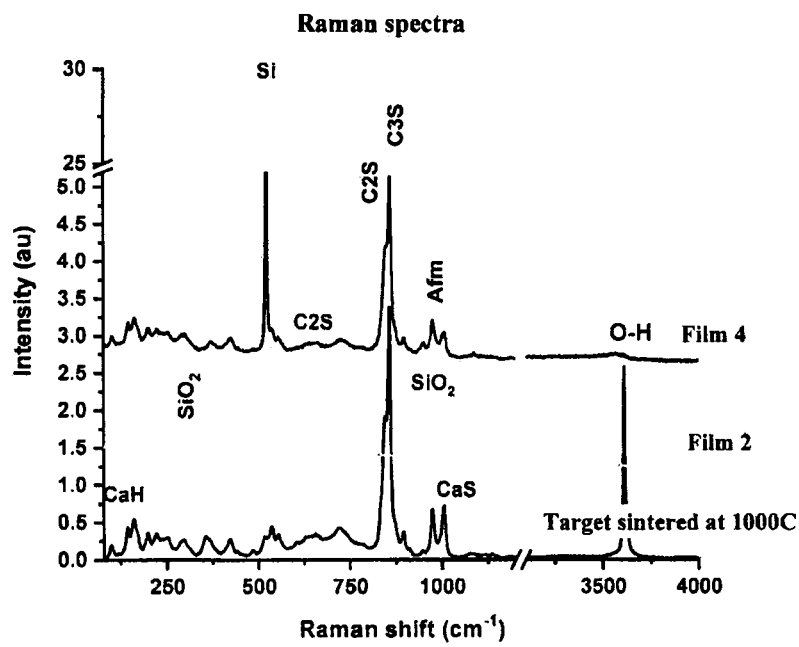
FIG. 14A includes Raman spectra, which confirms amorphous structure of films observed in FIG. 10A-B.
Figure 14B:
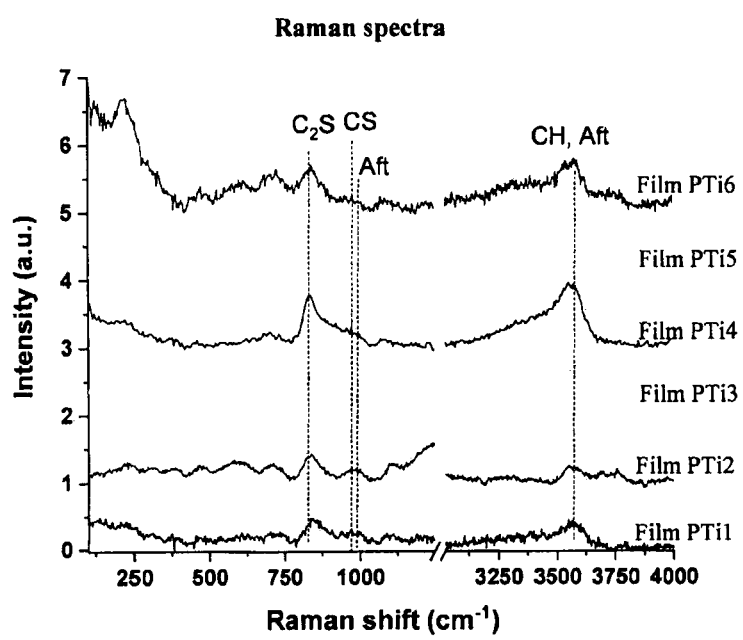
FIG. 14B includes Raman spectra, of films observed in FIG. 12A-B.
Figure 15A:
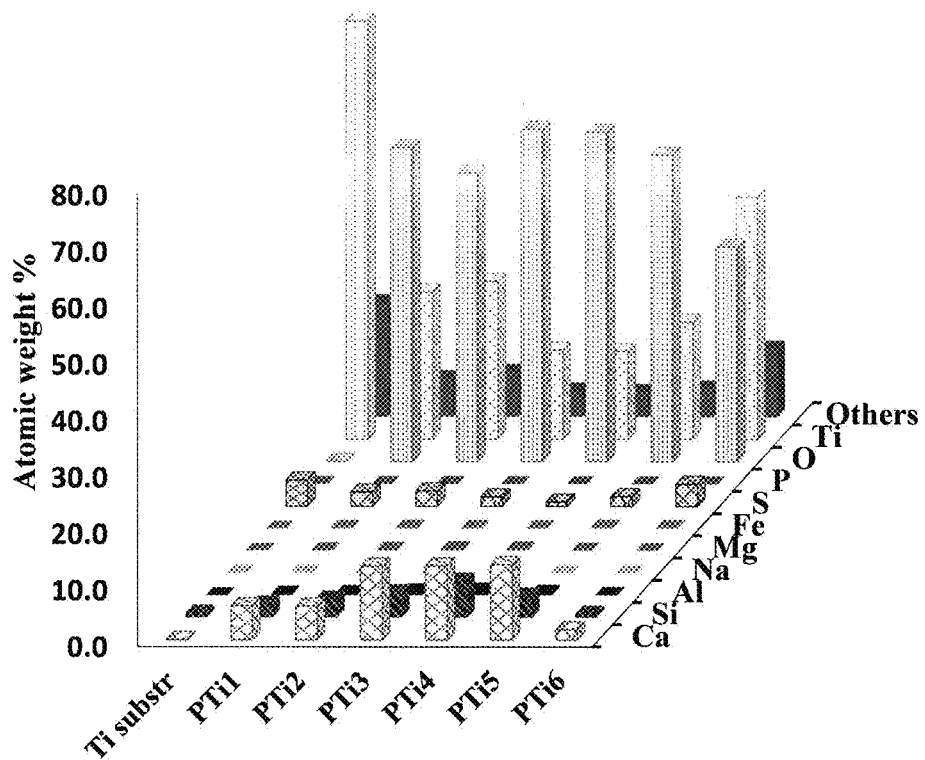
FIG. 15A includes a chart representing an EDS elemental analysis of films deposited on titanium implants using PLD process.
Figure 15B:
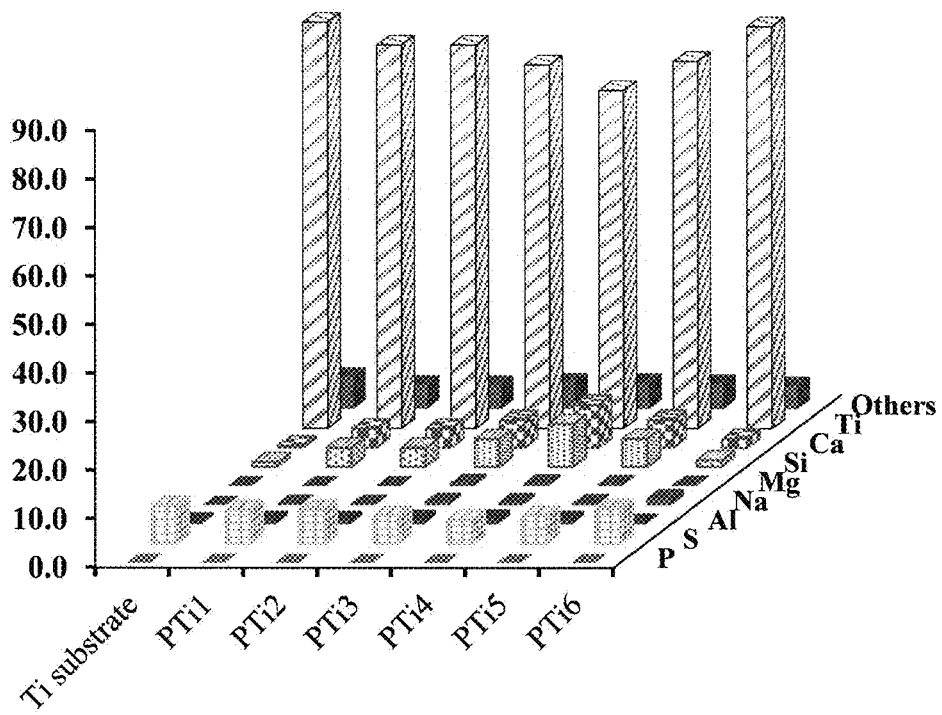
FIG. 15B includes a chart representing an XRF elemental analysis of films deposited on titanium implants using PLD process.

MTA films were deposited on Silicone (FIG. 10A), Gutta Percha (FIG. 11) and Titanium (FIG. 12A) samples using PLD. The thickness and degree of crystallinity of the film can be altered by laser power, laser pulse duration, number of pulses and sample temperature (FIGS. 10B and 12B). FIG. 10 B teaches a MTA biofunctional coating formed on a gutta percha point by a PLD process having a thickness of 338-522 nm. FIG. 12B teaches a MTA biofunctional coating formed on a titanium dental implant by a PLD process having a thickness of 50-1079 nm. To ensure that chemical composition of MTA material was not compromised during the whole way of processing (FIGS. 8 and 9), the full materials characterization of MTA materials was conducted at each stage of process. Scanning electron microscopy SEM was used to give a visualization of the films topography (FIGS. 10A, 11 and 12A). It could be seen that the films deposited on all types of samples (Si, gutta-percha and titanium) are amorphous with the particulates of crystalline chunks nucleated on the film surface or embedded in. The degree of crystallinity and phase analysis was determined by X-ray diffractometry. The XRD patterns (FIGS. 13A and B) shows that the deposited films have amorphous structure in general by and degree of crystallinity increases with the increase of laser power. The Raman spectroscopy shows the presence of tricalcium (C3S) and dicalcium (C2S) silicate phases in manner similar to the sintered target (FIGS. 14A and B). There were no significant changes in elemental composition were detected by EDS (FIG. 15A) and XRF (FIG. 15B) analysis during PLO deposition process.

Deposition of Films on Alternate Materials

PVD can also be used to deposit a thin layer of MTA on a variety of surfaces. Feasibility has been established for PVD of MTA on polyisoprene and ceramic surfaces. Other potential applications include deposition of a MTA film on variety of metal or ceramic surfaces such as titanium, NiTi alloys, stainless steel, and porcelain.

HA (Hydroxyapatite) Formation Study

In order to confirm bio-activity of sintered MTA and MTA coating produced by PVD the HA-forming ability was tested on sintered targets and films deposited on gutta-percha and titanium. The bioactivity of bone-bonding material is commonly evaluated in vitro by immersion of the test material into simulated body fluid (SBF) with ion concentrations nearly equal to those of human blood plasma, and examining the formation of hydroxyapatite (HA) on its surface.

Set of films, deposited on Gutta Percha and Titanium samples, were immersed in 2 ml of SBF (Dulbecco PBS 1×) at 37° C. for 1, 3, 7, 14 and 21 days. After immersion, the surface morphology of the samples and theirs composition were investigated by SEM, XRD, and EDS techniques. Based on reported studies, we expected the formation of HA after 3-7 days of immersion, the crystallized fraction HA commonly reported after 14-21 days. The typical sign of apatite formation is flower-like HA crystals observed by SEM. In addition to imaging the XRD and Raman analysis employed to determine the type of apatite forming. The major characteristic of appetites is Ca/P ratio that was determined by EDS analysis, the ratio 1.67 indicates the bone-like apatite formation.

Figure 16:
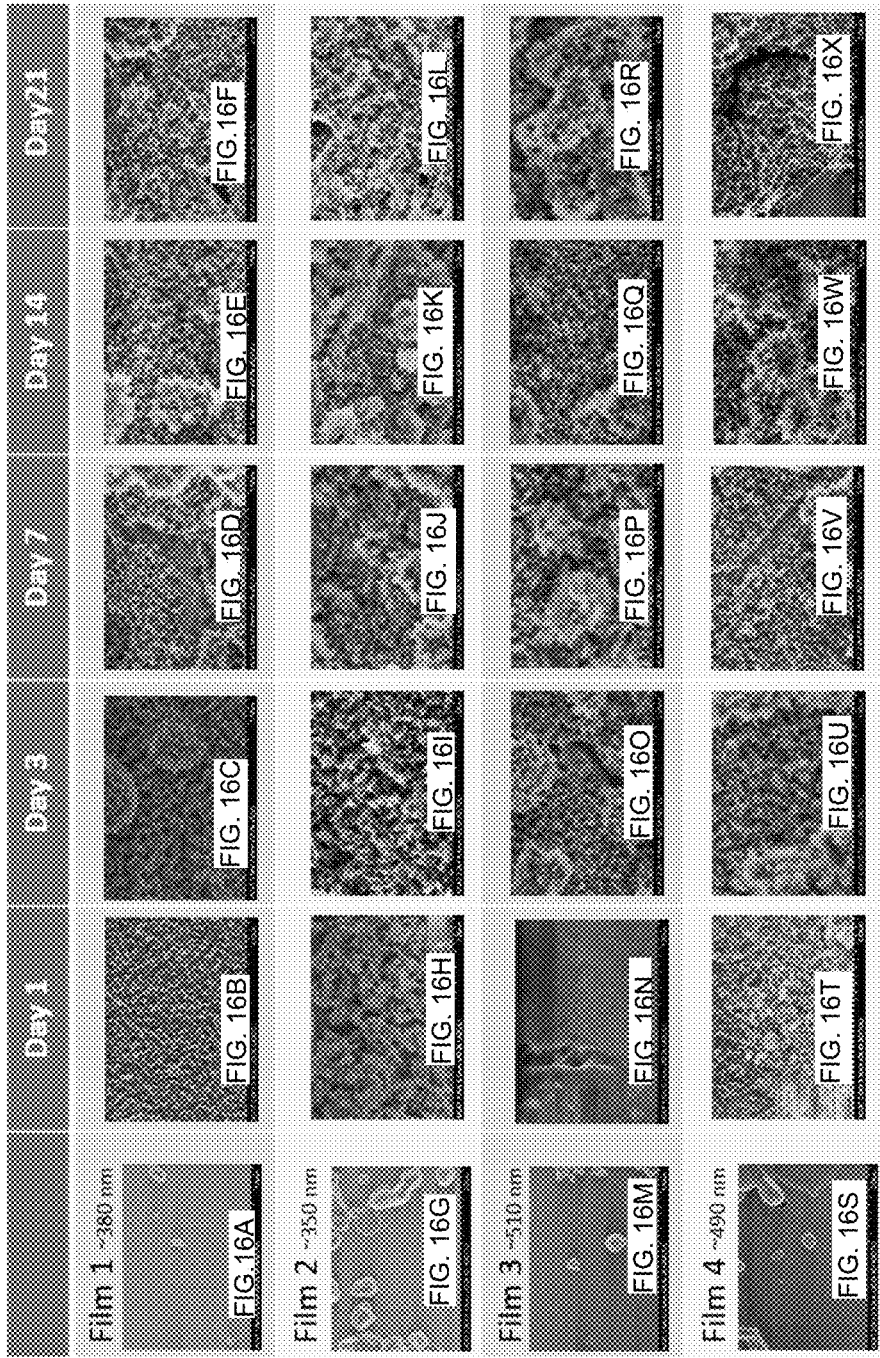
FIG. 16 includes the summary of SEM micrographs of MTA films deposited on gutta-percha points and subjected to the immersion in SBF. The micrographs (FIG. 16A-X) shows the formation of HA crystals for the days of immersion.
Figure 17:
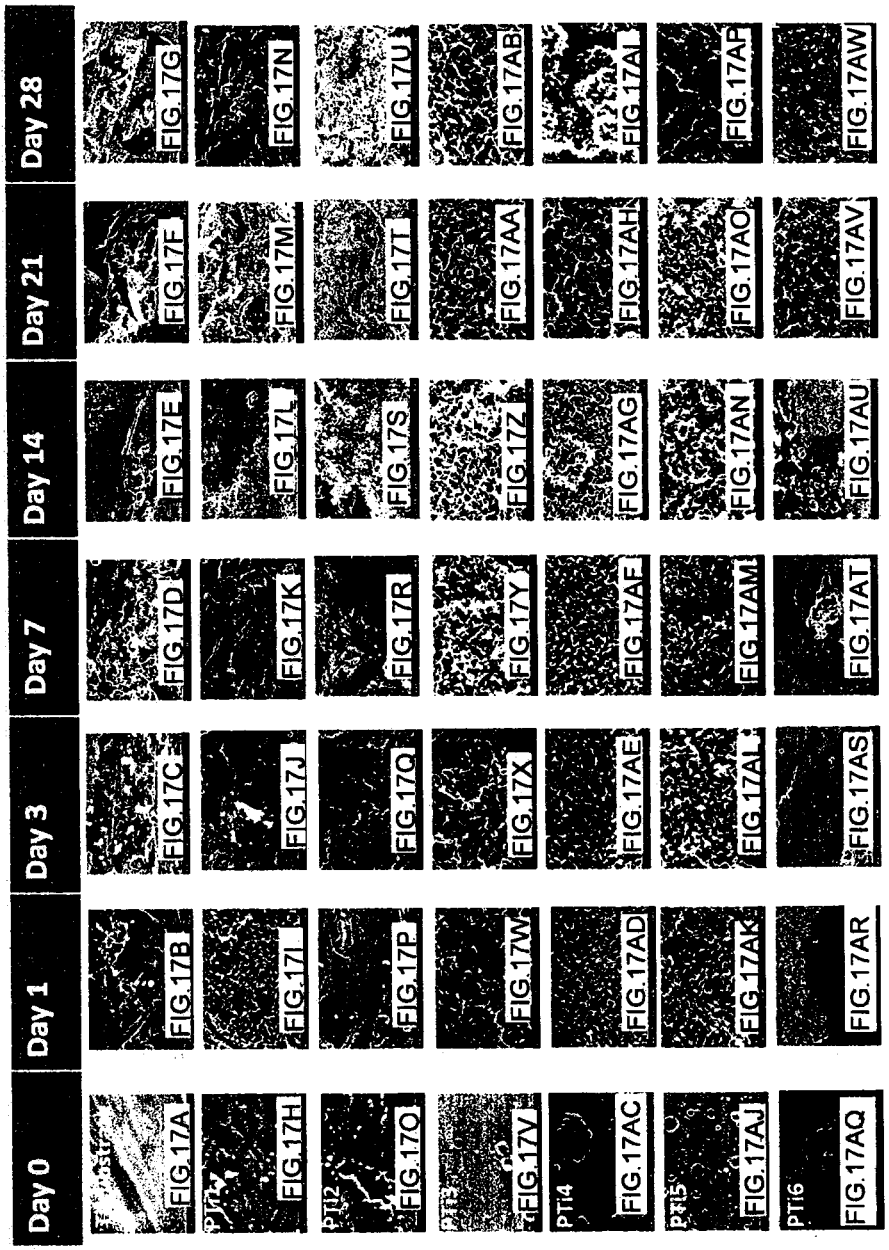
FIG. 17 includes the summary of SEM micrographs of MTA films deposited on titanium implants and subjected to the immersion in SBF. The micrographs (FIG. 17A-AW) shows the formation of HA crystals for the days of immersion.
Figure 18A:
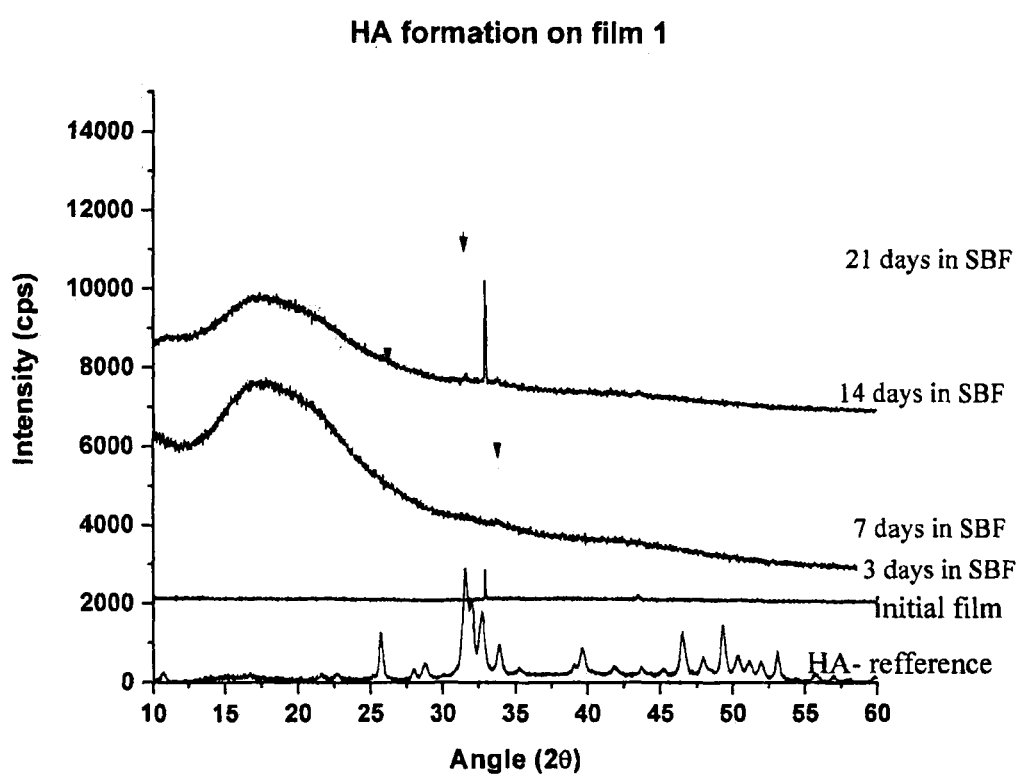
FIG. 18A depicts a chart representing XRD analysis of HA formation on MTA coating deposited on gutta-percha.
Figure 18B:
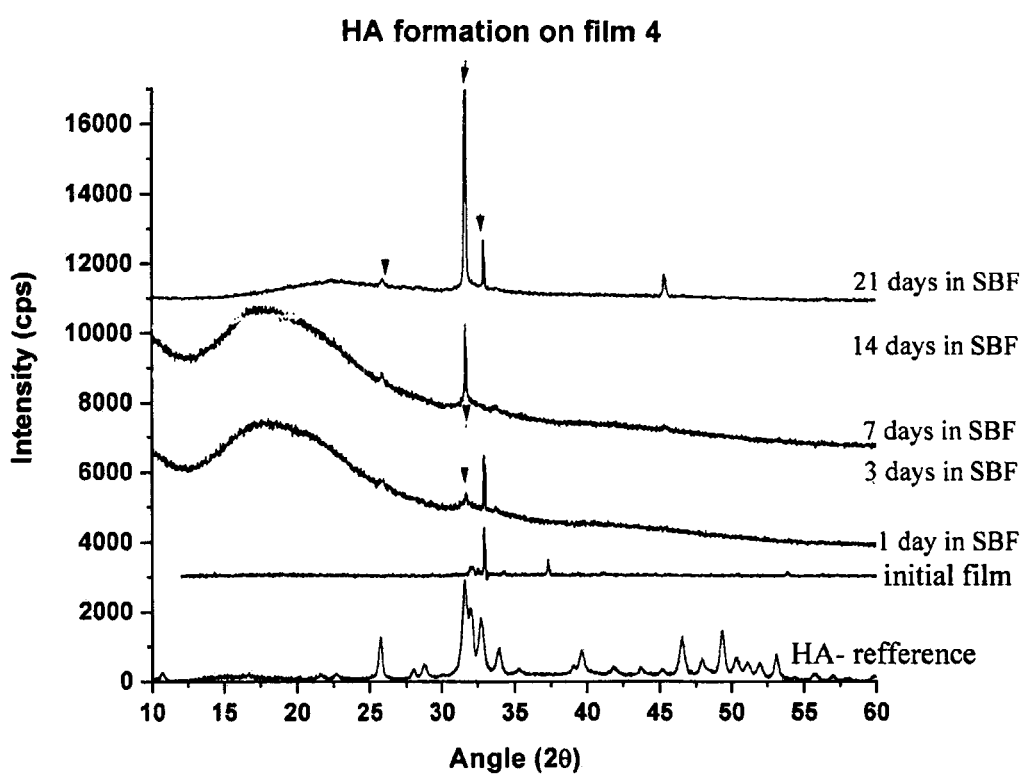
FIG. 18B depicts a chart representing XRD analysis of HA formation on MTA coating deposited on gutta-percha.
Figure 19:
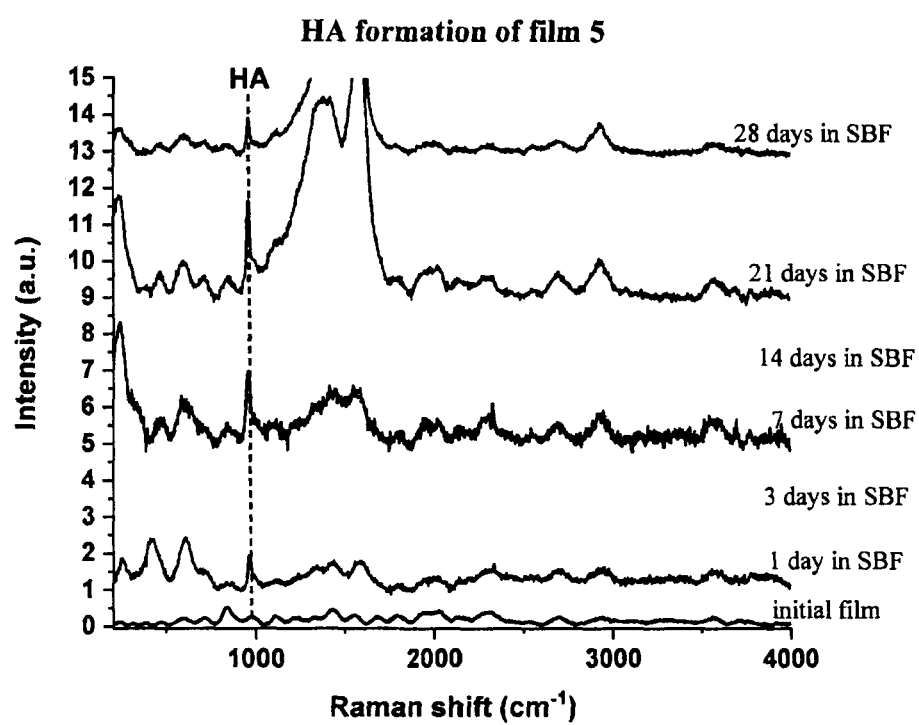
FIG. 19 shows Raman analysis of HA formation on MTA coating deposited on titanium.
Figure 20A:
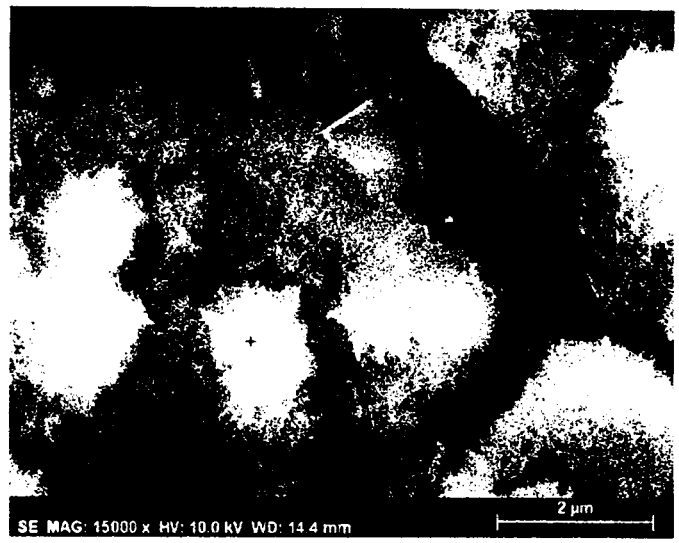
FIG. 20A includes SEM micrograph of the area analyzed with EDS spectra of HA formed on MTA coating deposited on gutta-percha after 21 day of immersion in SBF.
Figure 20:
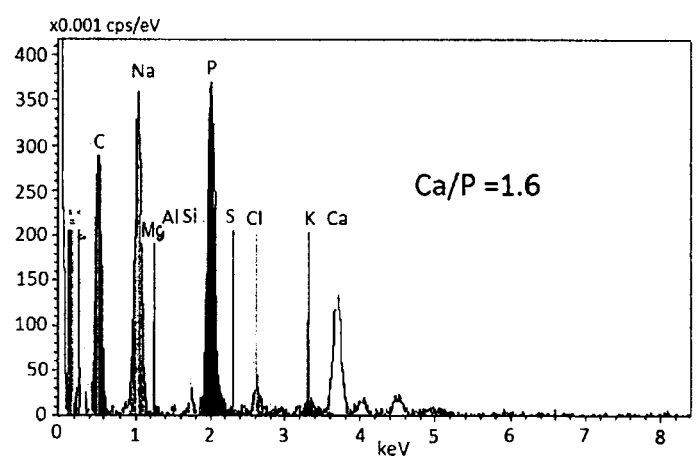
FIG. 20B includes a chart representing EDS spectra and analysis results of HA formed on MTA coating deposited on gutta-percha after 21 day of immersion in SBF.

The SEM images shown formation of HA-like crystals after 1 day immersion on films deposited on Gutta-percha (FIG. 16) and titanium samples (FIG. 17). The formation of HA after first day of immersion was also confirmed by XRD (FIGS. 18A and 18B) and Raman spectroscopy (FIG. 19). The Raman spectra and X-ray patterns were compared to the reference calcium phosphates: HA (obtained from Sigma-Aldridge), and mono-, di- and tri-calcium phosphates (obtained from MP Biomedicals). The Ca/P ratio of precipitated HA crystals was evaluated by EDS. FIGS. 20A-B represents the SEM image of MTA-coated gutta-percha sample after immersion, EDS spectra acquired from evaluated area and analysis results shown that Ca/P ratio in agreement with expected for HA. FIGS. 21 A-I represents the elemental map analysis recorded from MTA-coated titanium sample after immersion in SBF and shown the formation of HA crystals over the whole area of coated sample.

The similar bioactivity evaluation was conducted on sintered MTA-targets. The pressed and sintered samples were immersed in 10 ml of SBF (Dulbecco PBS 1×) at 37° C. for 1, 3, 7 and 14 days. The HA forming ability was evaluated by weight method comparing initial weights of samples and weight after immersion. The samples after immersion were air-dried at least for 24 hours before weighting. The graphical results of weight analysis are presented on FIGS. 7B-C. However the heat-treated (sintered) targets produces almost 10 times more HA per weight or surface area than pressed but not sintered MTA. The precipitation of HA crystals was observed by SEM after 1 day of immersion on all samples (FIG. 7A).

Thus, it should be evident that the invention as disclosed herein carries out one or more of the objects of the present invention set forth above and otherwise constitutes an advantageous contribution to the art. As will be apparent to persons skilled in the art, modifications can be made to the preferred embodiments disclosed herein without departing from the spirit of the invention, the scope of the invention herein being limited solely by the scope of the attached claims.

The invention claimed is:

1. An implantable dental device comprising a bio-functional coating of a mineral trioxide aggregate (MTA) material derived from a dense mineral trioxide aggregate (MTA) target; wherein the bio-functional coating of MTA is derived from the dense MTA target by processing of the dense MTA target: wherein the processing of the dense MTA target includes a physical vapor deposition process.

2. The implantable dental device according to claim 1, wherein said device is selected from gutta percha points and titanium implantable device.

3. The implantable dental device according to 2, wherein the thickness of the bio-functional coating on the gutta percha points is from 338 nm to 522 nm.

4. The implantable dental device according to claim 2, wherein the thickness of the bio-functional coating on the titanium implantable device is from 50 nm to 1079 nm.

5. The implantable dental device according to claim 1, wherein the dense MTA target is selected from a sintered MTA target or a hot isostatic pressing (HIP)-sintered MTA target.

6. The implantable dental device according to claim 5, wherein the sintered MTA target is produced by a process; said process comprising:
(i) mixing portland cement with deionized water having a ratio in the range of about 10:1 to about 1:10 to create a mixed cement;
(ii) curing the mixed cement in a mold to obtain a cured cement;
(iii) heating the cured cement in a post cure bake oven at a temperature from about 50° C. to about 500° C. to produce a post cure baked cement;
(iv) micronizing the post cure baked cement to a particle size ranging from about 1 micron to about 200 micron to form a micronized MTA;
(v) pressing the micronized MTA into a green compact using a hydraulic press with an applied pressure range from 60 Psi to 120 Psi;
(vi) heating the green compact in a sintering chamber to produce the sintered MTA target.

7. The implantable dental device according to claim 6, further comprising heating the sintered MTA target in a hot isostatic pressing (HIP) chamber at a temperature from about 25° C. to about 1500° C. to obtain the hot isostatic pressing (HIP)-sintered MTA target.

8. The implantable dental device according to claim 1, wherein the physical vapor deposition process includes one of cathodic arc deposition, electron beam physical vapor deposition, evaporative deposition, pulsed laser deposition or sputter deposition.

9. An implantable dental device comprising a bio-functional coating of a mineral trioxide aggregate (MTA) material derived from a dense mineral trioxide aggregate (MTA) target; wherein the bio-functional coating of MTA is derived from the dense MTA target by processing of the dense MTA target, wherein the processing of the dense MTA target includes (a) micronizing the dense MTA target to a particle size ranging from about 1 micron to about 200 microns to obtain a micronized dense MTA target; and (b) coating of micronized dense MTA target on a surface of dental device by compression molding, injection molding or powder spraying; wherein said device is selected from gutta percha points and titanium implantable device.

10. A method of forming a bio-functional coating of MTA material on a dental device, said method comprising:
(a) providing a dense MTA target; and
(b) processing of the dense MTA target to form the bio-functional coating of MTA material on a surface of dental device; wherein the processing of the dense MTA target includes a physical vapor deposition process.

11. The method according to claim 10, wherein the physical vapor deposition process includes one of cathodic arc deposition, electron beam physical vapor deposition, evaporative deposition, pulsed laser deposition or sputter deposition.

12. The method according to claim 10, wherein the dense MTA target is selected from sintered MTA target or hot isostatic pressing (HIP)-sintered MTA target.

13. The method according to claim 12, wherein the sintered MTA target is produced by process comprising:
(i) mixing portland cement with deionized water having a ratio in the range of about 10:1 to about 1:10 to create a mixed cement;
(ii) curing the mixed cement in a mold to obtain a cured cement;
(iii) placing the cured cement in a post cure bake oven at a temperature from about 50° C. to about 500° C. to produce a post cure baked cement;
(iv) micronizing the post cure baked cement to a particle size ranging from about 1 micron to about 200 micron to form a micronized MTA;
(v) pressing the micronized MTA into a green compact using a hydraulic press with an applied pressure range from 60 Psi to 120 Psi; and heating the green compact in a sintering chamber to produce the sintered MTA target.

14. The method according to claim 13, further comprising placing the sintered MTA target in a hot isostatic pressing (HIP) chamber at a temperature from about 250° C. to about 1500° C. to obtain hot isostatic pressing (HIP)-sintered MTA target.

15. A method of forming a bio-functional coating of MTA material on a dental device, said method comprising:
   (a) providing a dense MTA target: and
   (b) processing of the dense MTA target to form the bio-functional coating of MTA material on a surface of dental device; wherein the processing of the dense MTA target includes (i) micronizing the dense MTA target to a particle size ranging from about 1 micron to about 200 microns to obtain a micronized dense MTA target; and (ii) coating of micronized dense MTA target on a surface of dental device by compression molding, injection molding or powder spraying; wherein said device is selected from gutta percha points and titanium implantable device.

\* \* \* \* \*